(12) United States Patent
Park et al.

(10) Patent No.: US 11,895,911 B2
(45) Date of Patent: *Feb. 6, 2024

(54) ORGANIC LIGHT EMITTING DEVICE

(71) Applicant: LG Display Co., Ltd., Seoul (KR)

(72) Inventors: Heejun Park, Paju-si (KR); Seonkeun Yoo, Gunpo-si (KR); Soyoung Jang, Seoul (KR); Jicheol Shin, Gimpo-si (KR); Sangbeom Kim, Paju-si (KR); Sunghoon Kim, Seoul (KR); Tae Wan Lee, Seoul (KR); Dong Hun Lee, Seoul (KR); Jeonghoe Heo, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/978,065

(22) Filed: Oct. 31, 2022

(65) Prior Publication Data

US 2023/0172060 A1    Jun. 1, 2023

Related U.S. Application Data

(63) Continuation of application No. 16/721,777, filed on Dec. 19, 2019, now Pat. No. 11,515,480.

(30) Foreign Application Priority Data

Dec. 21, 2018    (KR) .................. 10-2018-0167668

(51) Int. Cl.
*H10K 85/60*    (2023.01)
*C07D 333/76*    (2006.01)
(Continued)

(52) U.S. Cl.
CPC ......... *H10K 85/636* (2023.02); *C07D 333/76* (2013.01); *H10K 85/633* (2023.02); *H01L 27/1255* (2013.01); *H01L 29/7869* (2013.01); *H10K 50/11* (2023.02); *H10K 50/15* (2023.02); *H10K 50/16* (2023.02); *H10K 50/17* (2023.02); *H10K 50/171* (2023.02); *H10K 50/844* (2023.02); *H10K 59/12* (2023.02); *H10K 71/00* (2023.02); *H10K 71/164* (2023.02);
(Continued)

(58) Field of Classification Search
None
See application file for complete search history.

(56) References Cited

U.S. PATENT DOCUMENTS 10,985,325 B2    4/2021  Kato et al.
2007/0012915 A1*  1/2007  Lee .................. H10K 85/631
                                                           257/40
(Continued)

FOREIGN PATENT DOCUMENTS

CN    104662010 A    5/2015
CN    106232768 A    12/2016
(Continued)

*Primary Examiner* — Gregory D Clark
(74) *Attorney, Agent, or Firm* — SEED IP LAW GROUP LLP

(57) ABSTRACT

The present disclosure provides an organic light-emitting device comprising a novel compound. When the novel compound is applied as a hole transport material to an organic light emitting device, the novel compound allows the device to have improved drive voltage, efficiency and lifespan characteristics.

10 Claims, 1 Drawing Sheet

(51) Int. Cl.

| | | |
|---|---|---|
| *H01L 27/12* | (2006.01) | |
| *H01L 29/786* | (2006.01) | |
| *H10K 50/11* | (2023.01) | |
| *H10K 50/15* | (2023.01) | |
| *H10K 50/16* | (2023.01) | |
| *H10K 50/17* | (2023.01) | |
| *H10K 50/844* | (2023.01) | |
| *H10K 59/12* | (2023.01) | |
| *H10K 71/00* | (2023.01) | |
| *H10K 71/16* | (2023.01) | |
| *H10K 102/00* | (2023.01) | |

(52) U.S. Cl.
CPC ....... *H10K 85/624* (2023.02); *H10K 85/6576* (2023.02); *H10K 2102/351* (2023.02)

(56) References Cited

U.S. PATENT DOCUMENTS

| | | |
|---|---|---|
| 2015/0034916 A1 | 2/2015 | Lee et al. |
| 2015/0263292 A1 | 9/2015 | Kato et al. |
| 2015/0280136 A1 | 10/2015 | Ryu et al. |
| 2016/0056387 A1 | 2/2016 | Kim et al. |
| 2016/0099420 A1 | 4/2016 | Itoi et al. |
| 2016/0133848 A1 | 5/2016 | Balaganesan et al. |
| 2018/0358562 A1 | 12/2018 | Takita et al. |
| 2020/0365814 A1 | 11/2020 | Ha et al. |

FOREIGN PATENT DOCUMENTS

| | | |
|---|---|---|
| CN | 106661445 A | 5/2017 |
| CN | 108369996 A | 8/2018 |
| CN | 108689913 A | 10/2018 |
| CN | 111217778 A | 6/2020 |
| CN | 111247652 A | 6/2020 |
| KR | 20140087883 A | 7/2014 |
| KR | 20150046069 A | 4/2015 |
| KR | 20150102734 A | 9/2015 |
| KR | 20160024625 A | 3/2016 |
| KR | 20170127353 A | 11/2017 |
| KR | 20170134163 A | 12/2017 |
| KR | 20180078177 A | 7/2018 |
| WO | WO 2017196081 A1 | 11/2017 |

* cited by examiner

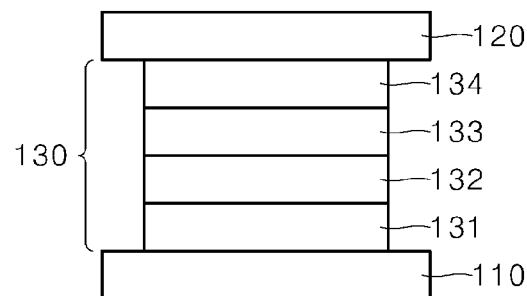
【FIG. 1】
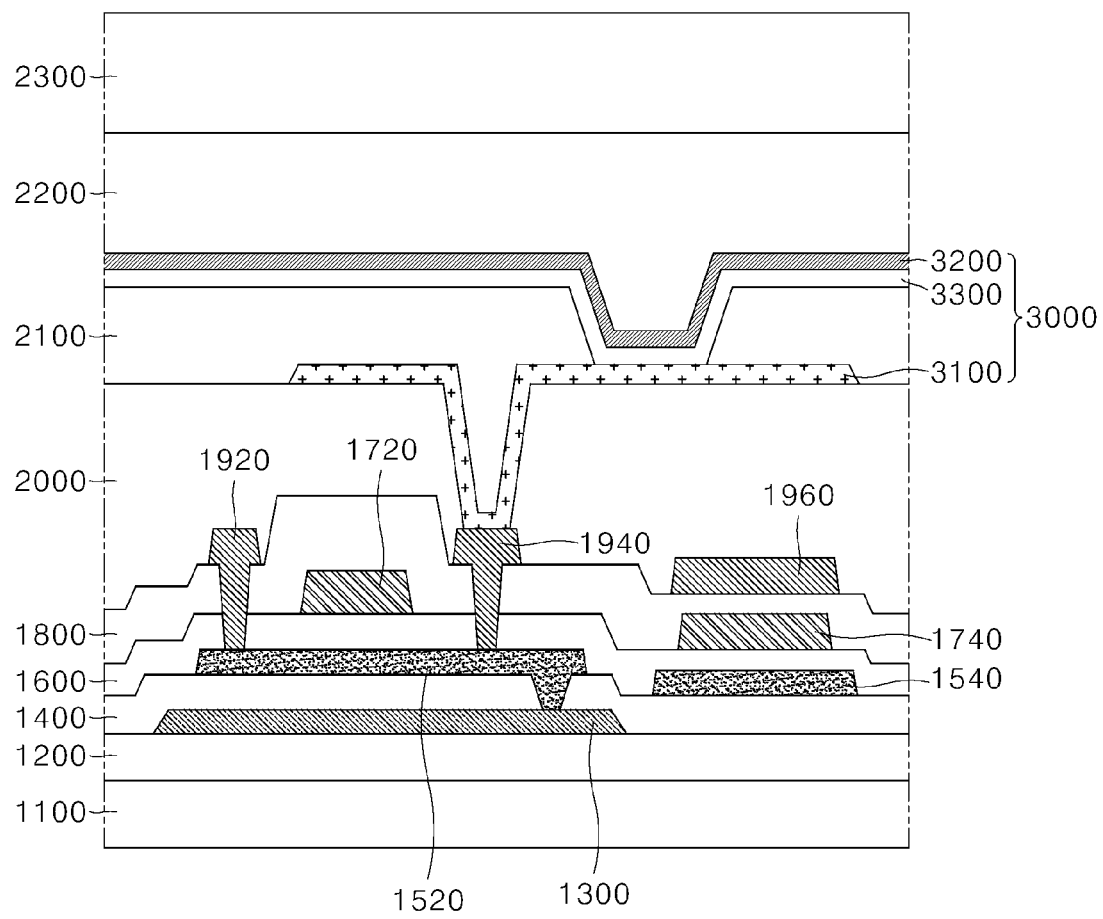
【FIG. 2】

ORGANIC LIGHT EMITTING DEVICE

CROSS-REFERENCE TO RELATED APPLICATIONS

This application is a continuation of U.S. patent application Ser. No. 16/721,777, filed Dec. 19, 2019 which claims the priority of Korean Patent Application No. 10-2018-0167668, filed on Dec. 21, 2018, in the Korean Intellectual Property Office, the disclosures of which are hereby incorporated by reference in their entireties.

BACKGROUND

Technical Field

The present disclosure relates to a novel compound and an organic light-emitting device comprising the same.

Description of the Related Art

As a display device becomes larger recently, a flat display device with good space utilization is getting more attention. One of such flat display devices may include an organic light-emitting display device including an organic light-emitting diode (OLED). The organic light-emitting display device is rapidly developing.

In the organic light-emitting diode (OLED), when charges are injected into a light-emitting layer formed between a first electrode and a second electrode to form paired electrons and holes top to form excitons, exciton energy is converted to light for emission. The organic light emitting diode may be driven at a lower voltage and has a relatively low power consumption than a conventional display device. The organic light emitting diode may have advantages of having excellent color rendering and being able to be applied to a flexible substrate for various applications.

BRIEF SUMMARY

One purpose of the present disclosure is to provide a novel compound of a novel structure that is stable materially and has high hole mobility.

Another purpose of the present disclosure is to develop an organic light-emitting device with high efficiency, low power consumption and long lifespan by applying the novel compound to a hole transport layer or an auxiliary hole transport layer of the organic light-emitting device.

The purposes of the present disclosure are not limited to the above-mentioned purposes. Other purposes and advantages of the present disclosure, as not mentioned above, may be understood from the following descriptions and more clearly understood from the embodiments of the present disclosure. Further, it will be readily appreciated that the objects and advantages of the present disclosure may be realized by features and combinations thereof as disclosed in the claims.

According to an aspect of the present disclosure, there is provided a compound represented by the following Chemical Formula 1:

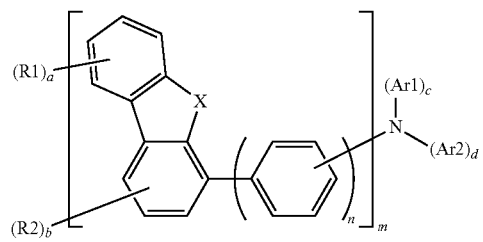

Chemical Formula 1 where, in the Chemical Formula 1,
X represents O or S,
each of R1 and R2 independently represents a substituent selected from the group consisting of an aryl group having 6 to 30 carbon atoms, a heteroaryl group having 5 to 30 carbon atoms, an alkyl group having 1 to 15 carbon atoms, a halogen atom, and a deuterium atom,
a is an integer from 0 to 4, when a is 2 or more, R1s are the same as or different from each other, and adjacent R1s may be bonded to each other to form a ring,
b is an integer from 0 to 3, when b is 2 or more, R2s are the same as or different from each other, and adjacent R2s may be bonded to each other to form a ring,
n is 0 or 1, n=0 representing a direct bond,
m is an integer from 1 to 3,
each of c and d is an integer of 0 or 1,
m, c, and d are selected such that when m is 1, c+d=2, when m is 2, c+d=1, and when m is 3, c+d=0, and
each of Ar1 and Ar2 independently represents one selected from the group consisting of a substituted or unsubstituted aryl group having 6 to 30 carbon atoms, an alkyl group having 1 to 30 carbon atoms, an alkenyl group having 2 to 30 carbon atoms, an alkynyl group having 2 to 20 carbon atoms, an alkoxyl group having 1 to 30 carbon atoms, and an aryloxy group having 6 to 30 carbon atoms.

In another aspect of the present disclosure, there is provided an organic light-emitting device that includes a first electrode, a second electrode, and at least one organic material layer between the first and second electrodes, wherein the organic material layer contains the compound represented by the Chemical Formula 1.

The organic light-emitting device according to the present disclosure may have improved drive voltage, efficiency and lifespan.

Further specific effects of the present disclosure as well as the effects as described above will be described in conjunction with illustrations of specific details for carrying out the present disclosure.

BRIEF DESCRIPTION OF THE DRAWINGS

FIG. 1 is a schematic cross-sectional view of an organic light-emitting device incorporating the compound represented by the Chemical Formula 1 according to one embodiment of the present disclosure.

FIG. 2 is a schematic cross-sectional view of an organic light-emitting display device employing the organic light-emitting device according to another implementation of the present disclosure.

DETAILED DESCRIPTION

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first," "second," "third," and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a term "substituted" means that a hydrogen atom has been substituted.

As used herein, a substituent in the term "substituted" may include one selected from the group consisting of, for example, deuterium, tritium, an alkyl group of 1 to 20 carbon atoms unsubstituted or substituted with halogen, an alkoxy group having 1 to 20 carbon atoms unsubstituted or substituted with halogen, halogen, a cyano group, a carboxy group, a carbonyl group, an amine group, an alkylamine group having 1 to 20 carbon atoms, a nitro group, an alkylsilyl group having 1 to 20 carbon atoms, an alkoxysilyl group having 1 to 20 carbon atoms, a cycloalkylsilyl group having 3 to 30 carbon atoms, an arylsilyl group having 6 to 30 carbon atoms, an aryl group having 6 to 30 carbon atoms, an arylamine group having 6 to 20 carbon atoms, a heteroaryl group having 4 to 30 carbon atoms, and a combination thereof. However, the present disclosure is not limited thereto.

As used herein, a term "alkyl" means any alkyl including a straight chain alkyl, and branched chain alkyl.

As used herein, a term "heterocyclic ring" includes a hetero aromatic ring and a hetero alicyclic ring. Each of the "hetero aromatic ring" and the "hetero alicyclic ring" may contain a single ring or a polycyclic ring.

As used herein, the term "hetero" as used in the term "heteroaryl group" means that one or more carbon atoms, for example, 1 to 5 carbon atoms among carbon atoms constituting the aromatic ring are substituted with at least one hetero atom selected from the group consisting of N, O, S and combinations thereof.

As used herein, the phase "combination thereof" as used in the definition of the substituent means that two or more substituents are bonded to each other via a linking group or two or more substituents are bonded to each other via condensation, unless otherwise defined.

Hereinafter, the present disclosure describes a novel compound according to some embodiments of the present disclosure, and an organic light emission device including the compound.

According to one implementation of the present disclosure, there is provided a compound represented by the following Chemical Formula 1:

Chemical Formula 1

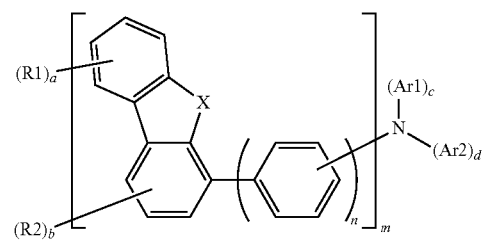

where, in the Chemical Formula 1,
X represents O or S,
each of R1 and R2 independently represents a substituent selected from the group consisting of an aryl group having 6 to 30 carbon atoms, a heteroaryl group having 5 to 30 carbon atoms, an alkyl group having 1 to 15 carbon atoms, a halogen atom, and a deuterium atom, a is an integer from 0 to 4, when a is 2 or more, R1s are the same as or different from each other, and adjacent R1s may be bonded to each other to form a ring, b is an integer from 0 to 3, when b is 2 or more, R2s are the same as or different from each other, and adjacent R2s may be bonded to each other to form a ring, n is 0 or 1, n=0 representing a direct bond, m is an integer from 1 to 3, each of c and d is an integer of 0 or 1, m, c, and d are selected such that when m is 1, c+d=2, when m is 2, c+d=1, and when m is 3, c+d=0, and each of Ar1 and Ar2 independently represents one selected from the group consisting of a substituted or unsubstituted aryl group having 6 to 30 carbon atoms, an alkyl group having 1 to 30 carbon atoms, an alkenyl group having 2 to 30 carbon atoms, an alkynyl group having 2 to 20 carbon atoms, an alkoxyl group having 1 to 30 carbon atoms, and an aryloxy group having 6 to 30 carbon atoms.

When the adjacent R1s are bonded to each other to form a ring, the ring may include a C5 to C30 alicyclic or C6 to C30 aromatic, single or polycyclic ring-based, saturated or unsaturated ring.

When the adjacent R2s are bonded to each other to form a ring, the ring may include a C5 to C30 alicyclic or C6 to C30 aromatic, single or polycyclic ring-based, saturated or unsaturated ring.

In one implementation, the compound represented by the Chemical Formula 1 may be represented by a following Chemical Formula 2.

Chemical Formula 2

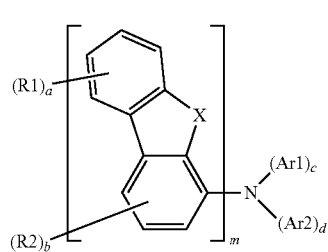

where, in the Chemical Formula 2, definitions of R1, R2, X, Ar1, Ar2, a, b, c and d, m are the same as in the Chemical Formula 1, respectively.

In the Chemical Formula 1, a bond position of phenylene may be an ortho, meta or para position. Specifically, the compound represented by the Chemical Formula 1 may be represented by any one of the following Chemical Formula 3 to Chemical Formula 5.

Chemical Formula 3

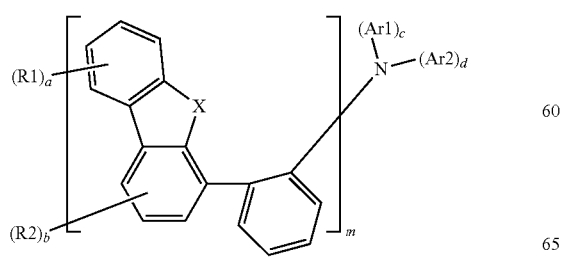

Chemical Formula 4

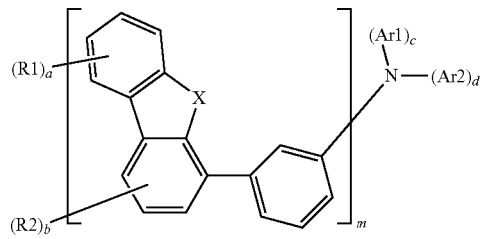

Chemical Formula 5

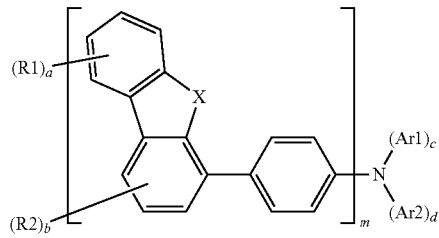

where, in each of the Chemical Formulas 3 to 5, definitions of R1, R2, X, Ar1, Ar2, a, b, c and d, m are the same as in the Chemical Formula 1, respectively.

In one embodiment, each of Ar1 and Ar2 of the Chemical Formula 1 may be selected from following substituents.

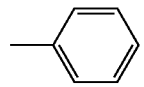

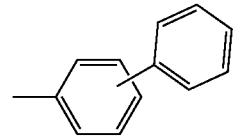

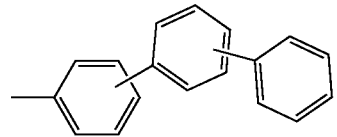

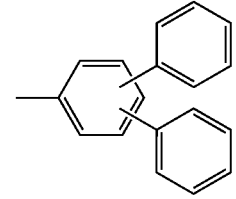

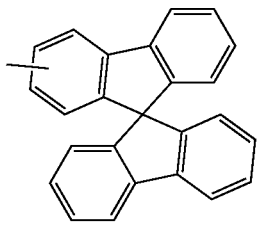

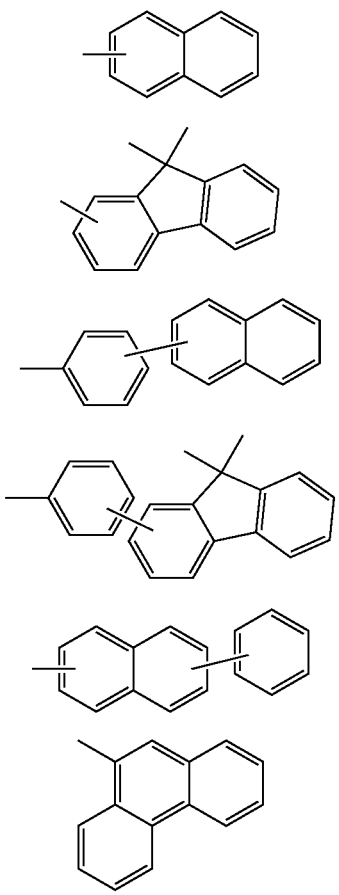

The compound represented by the Chemical Formula 1 has excellent hole transport characteristics and material stability, thereby to lower a device drive voltage, and to improve efficiency, and power consumption when the compound is applied to an organic light-emitting device. Further, when the compound is applied to the organic light-emitting device, the organic light-emitting device has high thermal and electrical stability to have a long lifespan.

The compound may be applied to a hole transport layer or an auxiliary hole transport layer of an organic light-emitting device.

In one implementation, the compound represented by the Chemical Formula 1 is free of a carbazole group. Specifically, in the compound represented by the Chemical Formula 1, each of R1, R2, Ar1 and Are is not carbazole or free of carbazole. Amine derivatives containing carbazole as a previously known hole transport material have a disadvantage that the hole mobility therein is low such the device efficiency is low and power consumption is high. In one implementation, the compound represented by the Chemical Formula 1 is an amine derivative excluding the carbazole and has a framework structure contributing to the hole mobility. Thus, the compound represented by the Chemical Formula 1 realizes high hole mobility, thus improving power consumption when the compound is applied to the organic light-emitting device.

Further, a framework structure of the compound represented by the Chemical Formula 1 is a structure of an amine compound having dibenzothiophene or dibenzofuran introduced thereto, and has an advantage in improving power consumption via high hole mobility, and the device efficiency and lifespan.

Therefore, in one implementation, the compound represented by the Chemical Formula 1 contains a non-carbazole-based amine derivative as a hole transport material, but has a high hole mobility characteristic. Thus, the compound represented by the Chemical Formula 1 can lower the device drive voltage. A fused ring structure of a core in the compound is a novel structure in a hole transport material and thus may contribute to implementation of a thermally and electrically stable device.

Specifically, the compound represented by the Chemical Formula 1 may be represented by any one of following 64 Chemical Formulas:

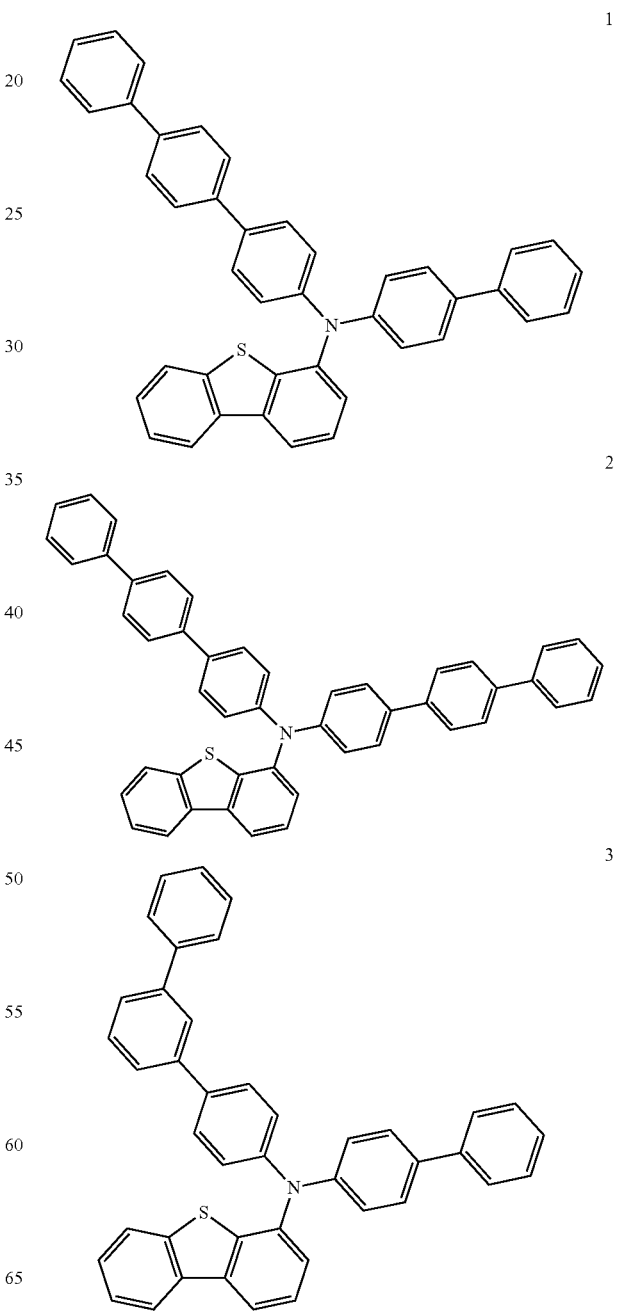

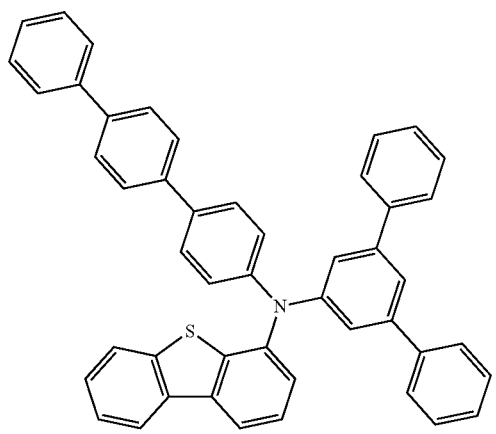
4
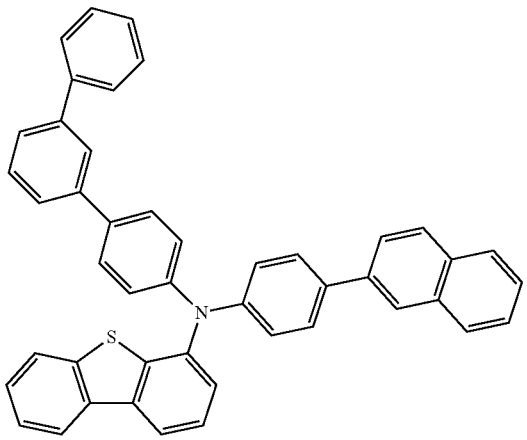
7
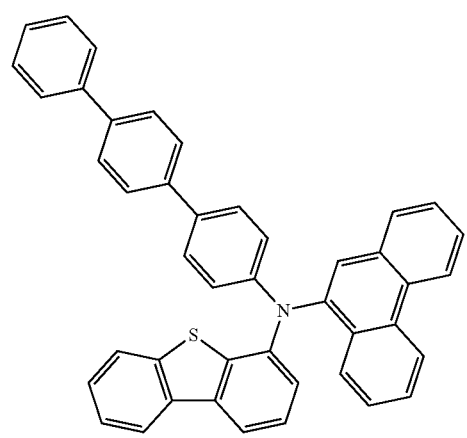
5
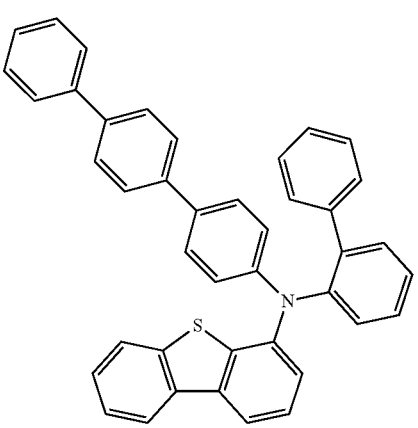
8
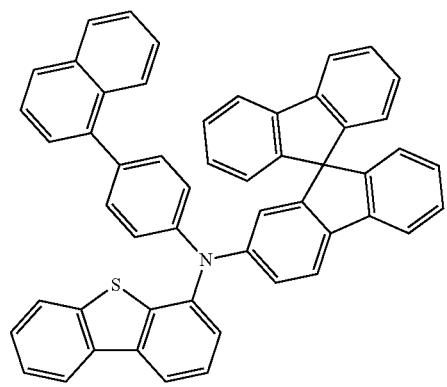
6
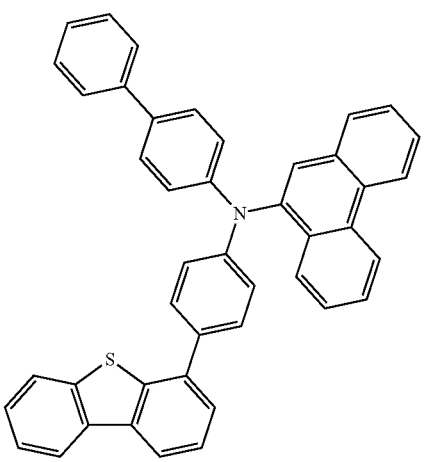
9

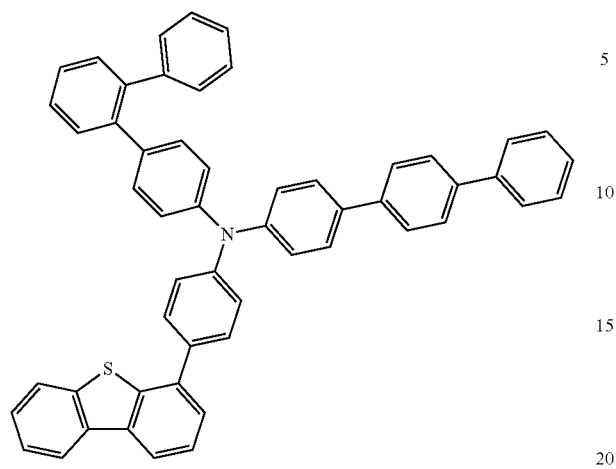
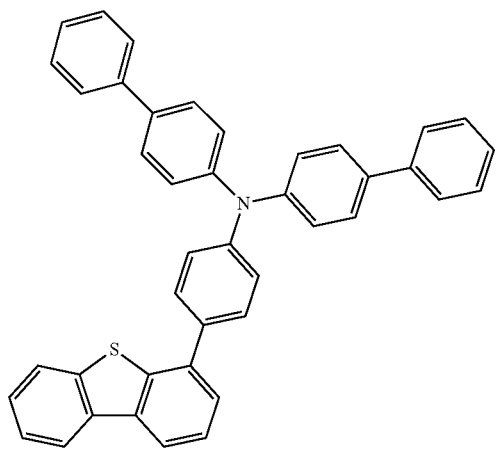
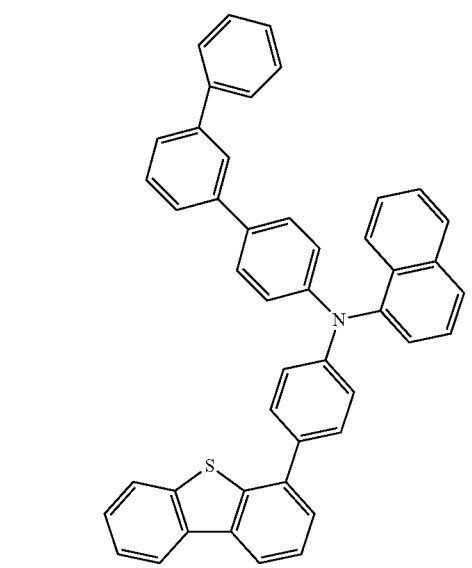
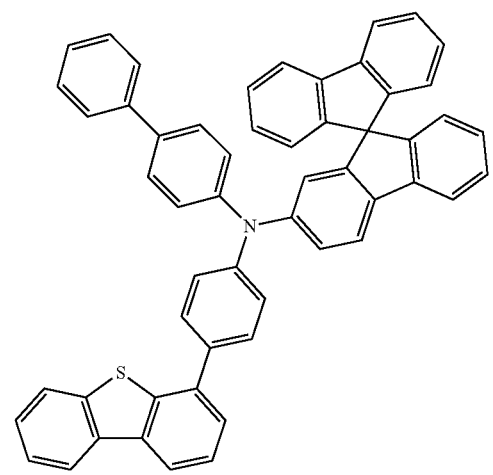
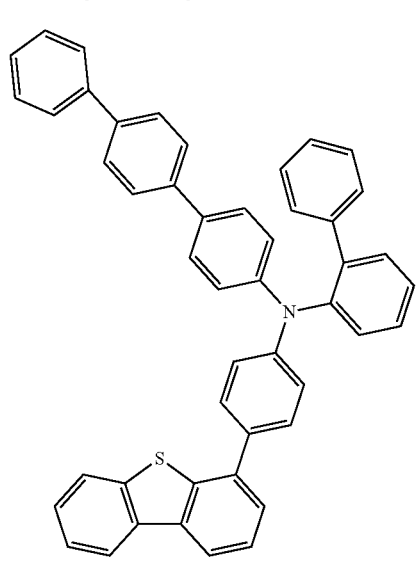
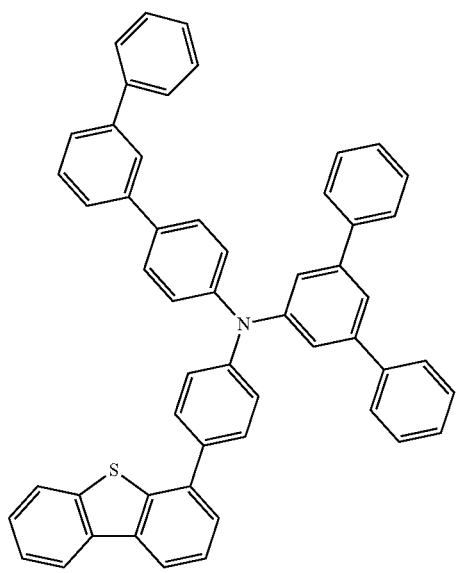

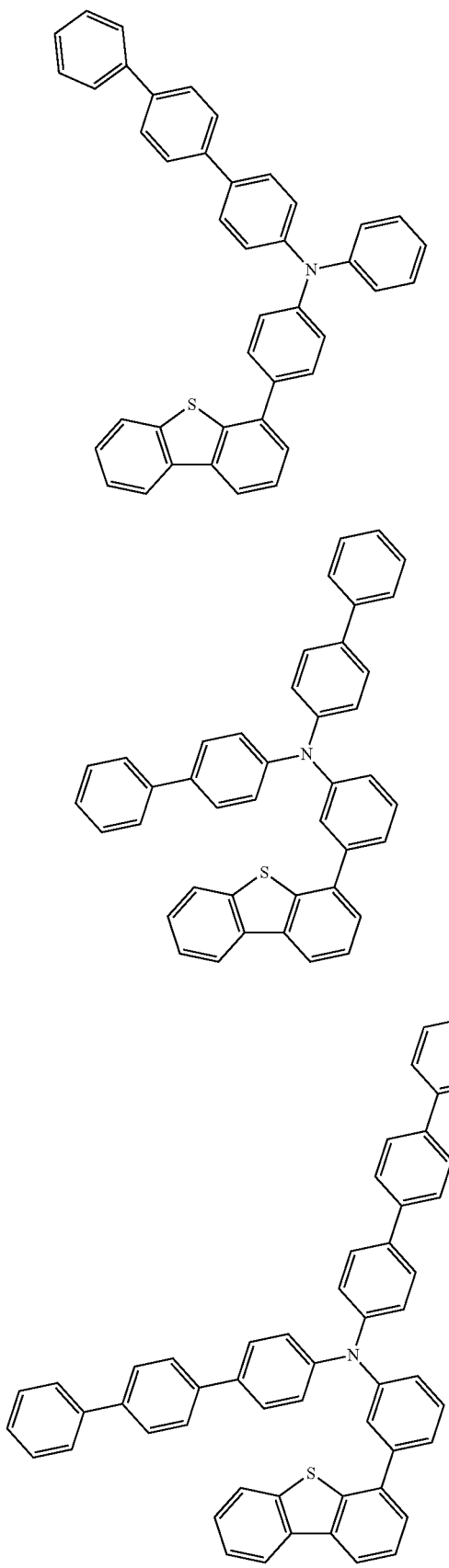
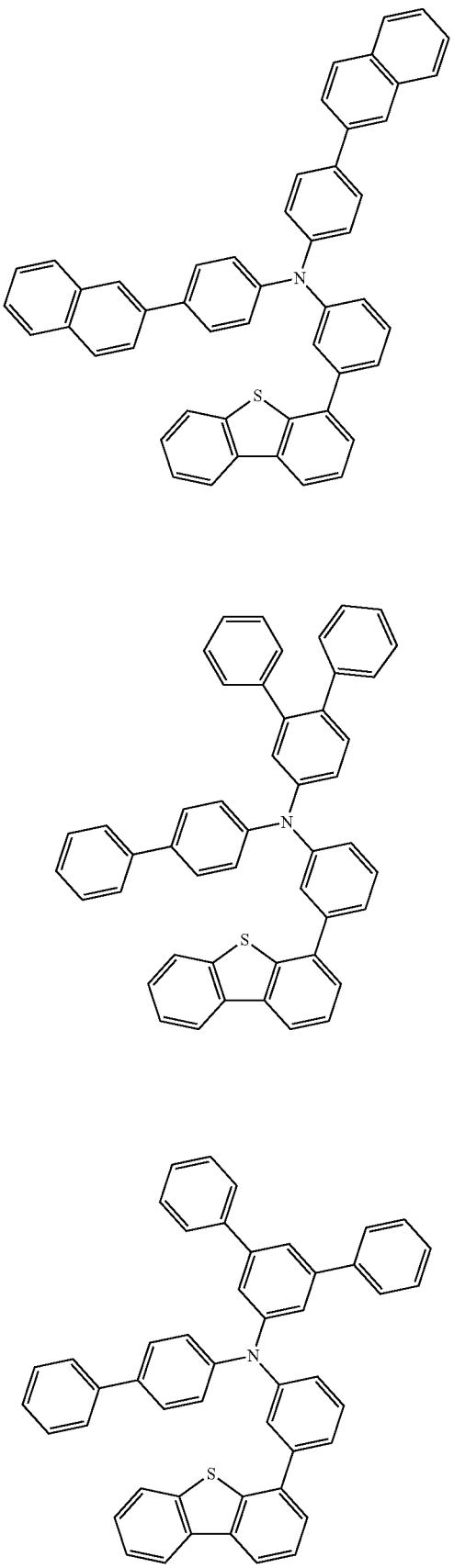

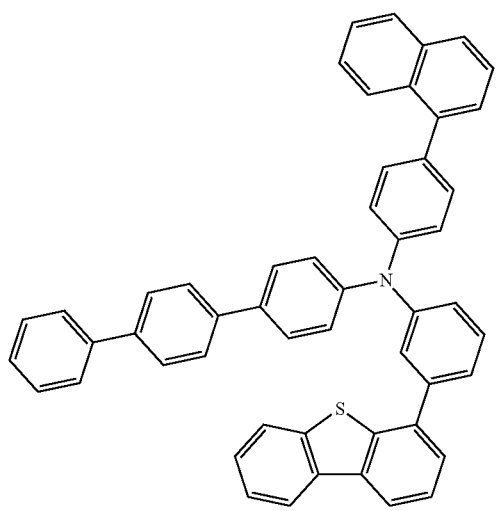
22
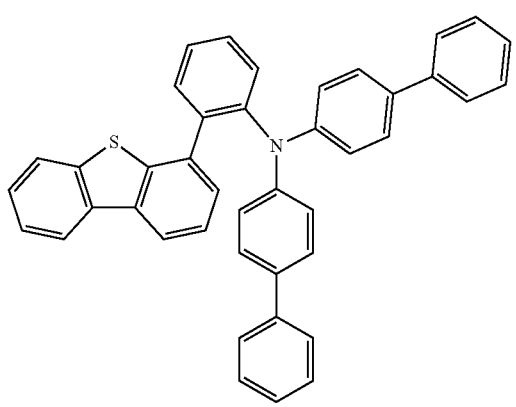
25
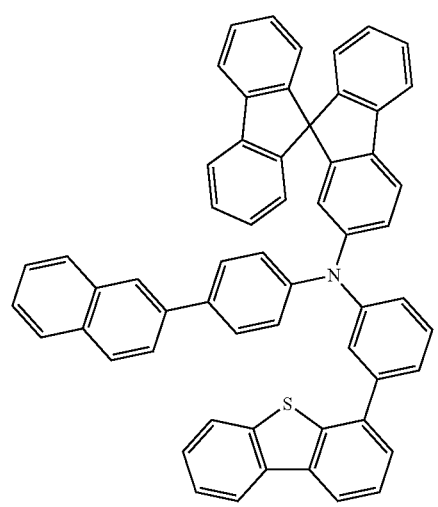
23
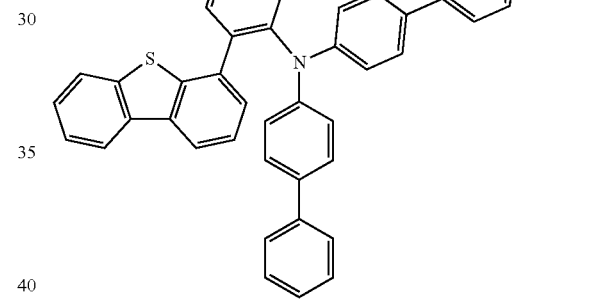
26
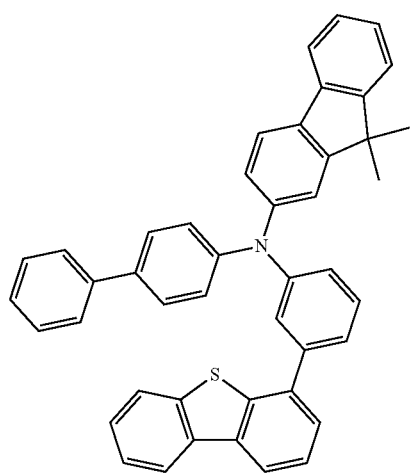
24
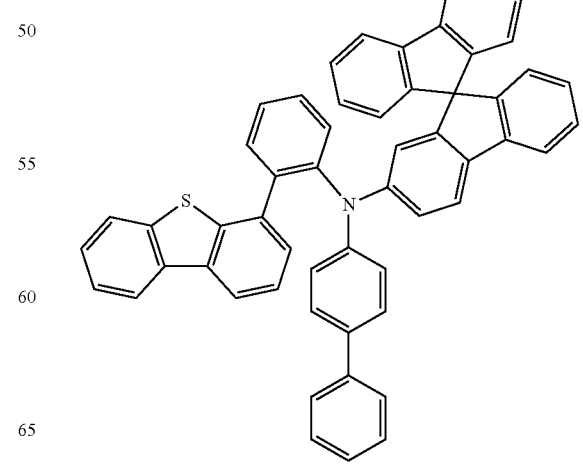
27

28
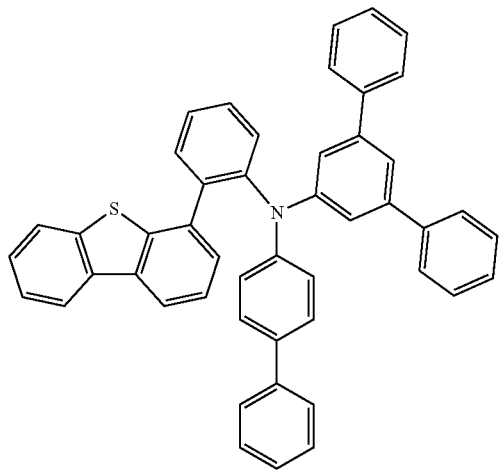
29
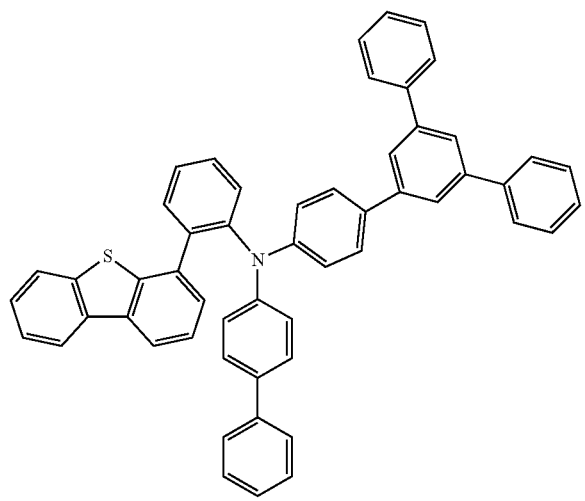
30
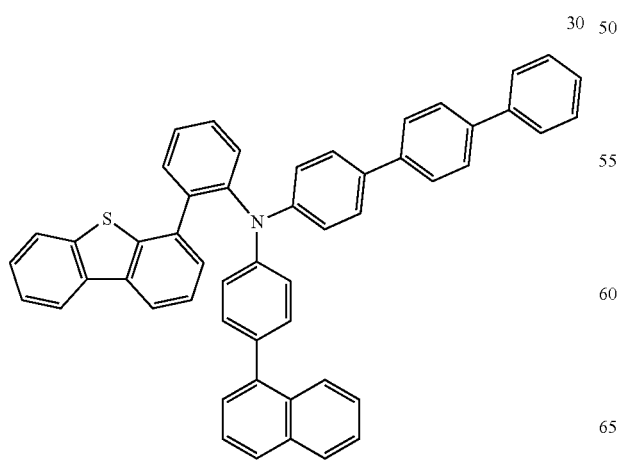
31
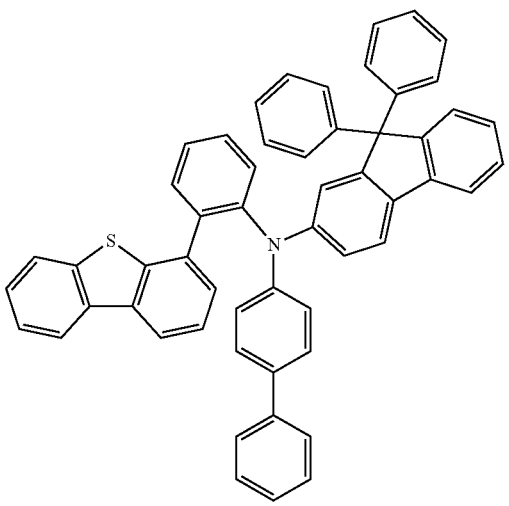
32
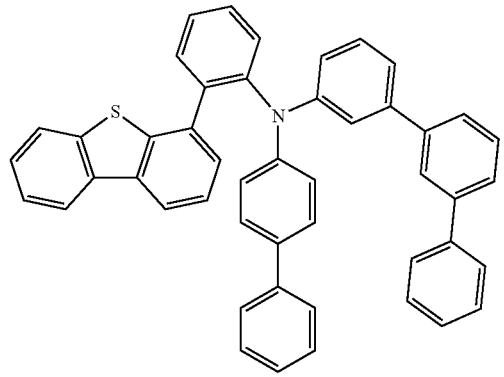
33
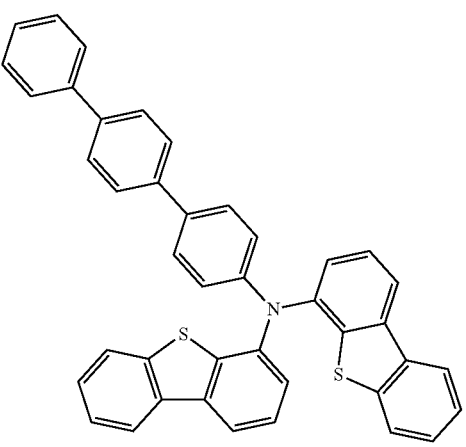

34
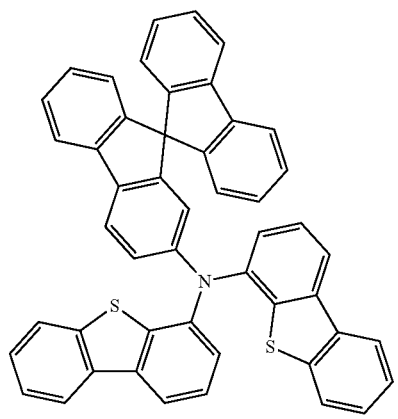
35
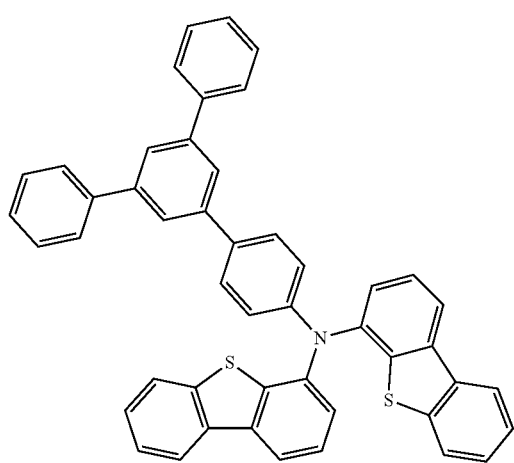
36
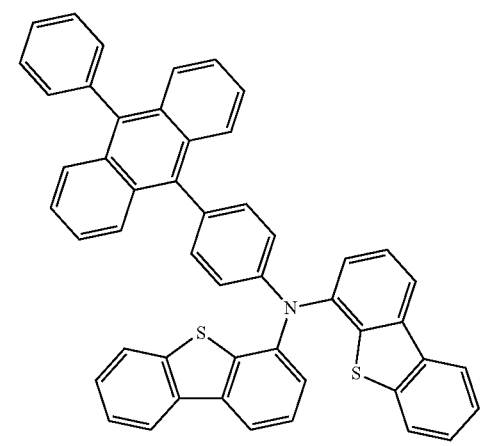
37
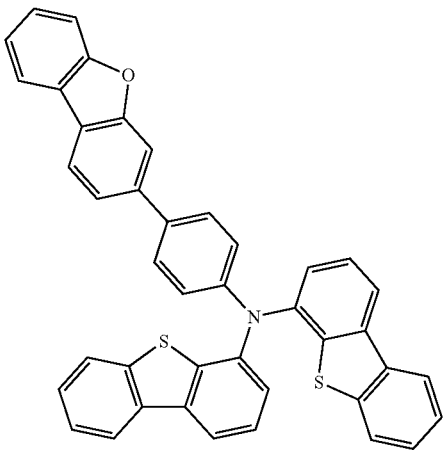
38
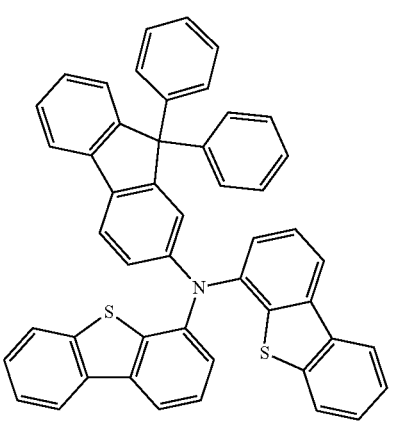
39
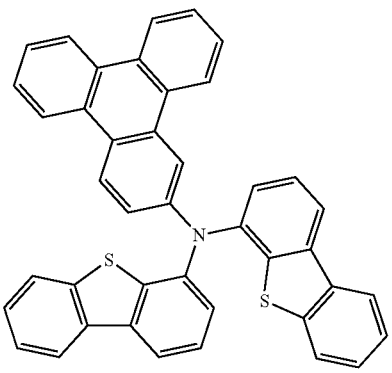
40
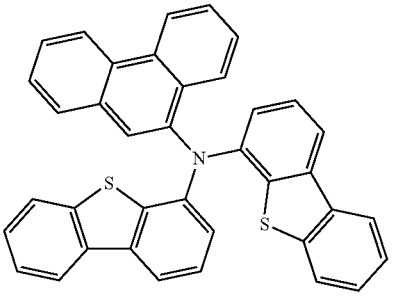

41
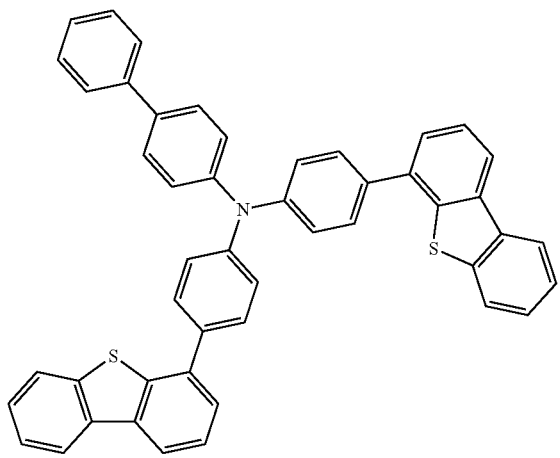
42
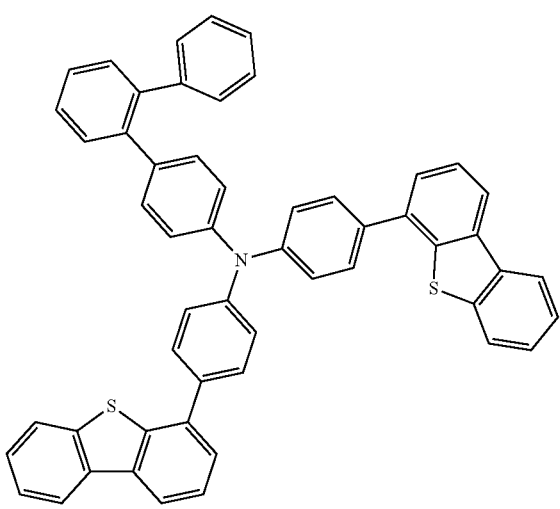
43
44
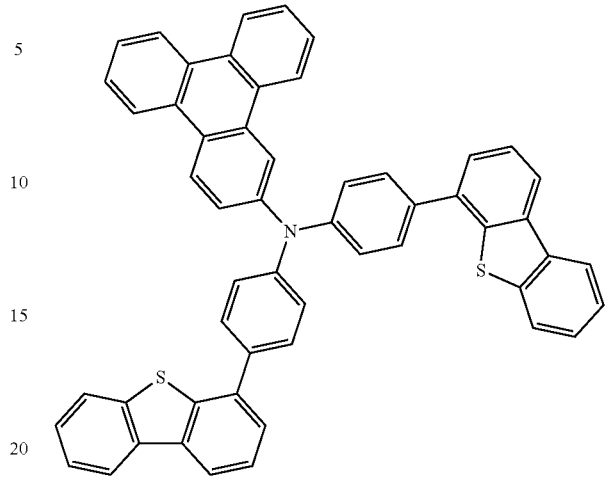
45
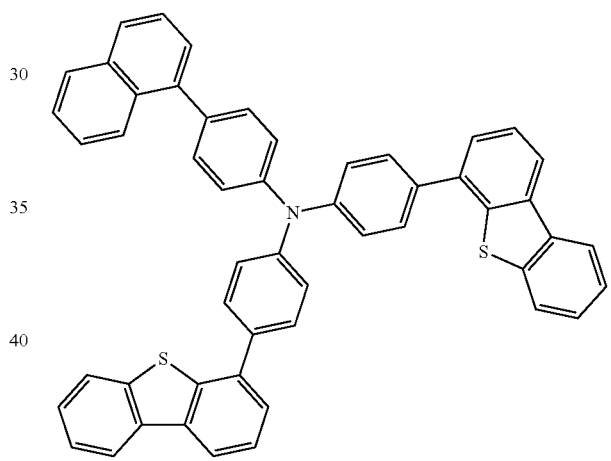
46
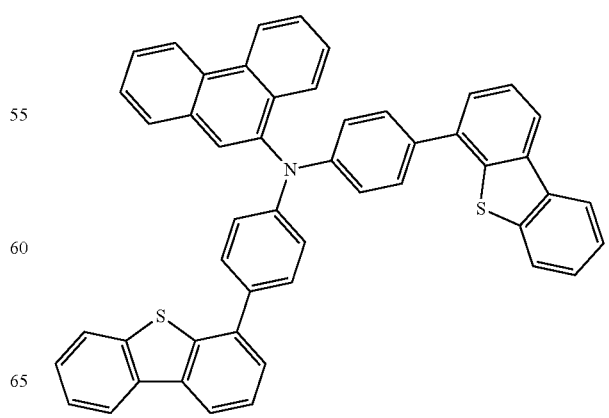

47
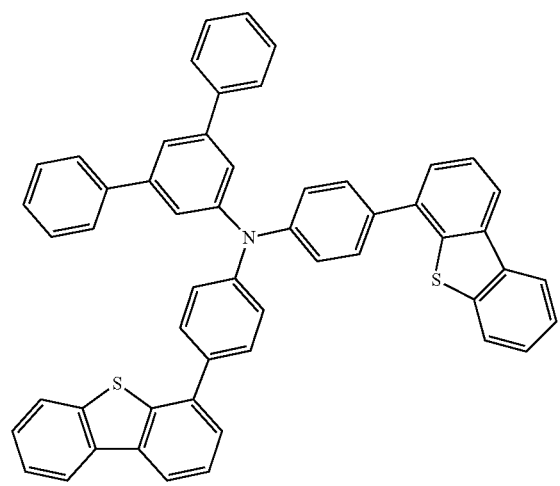
48
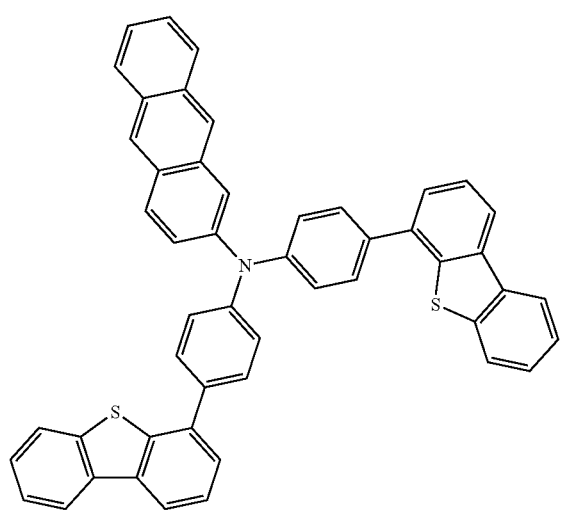
49
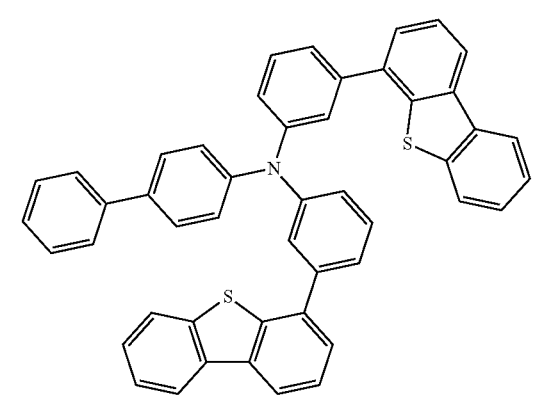
50
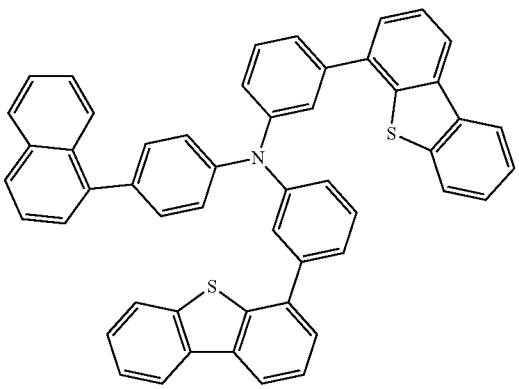
51
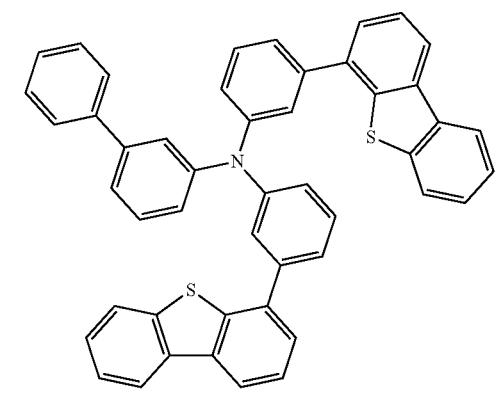
52
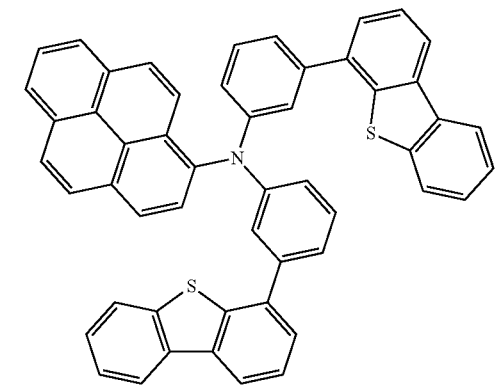
53
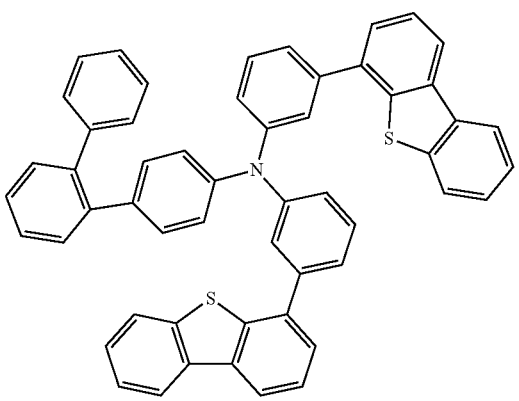

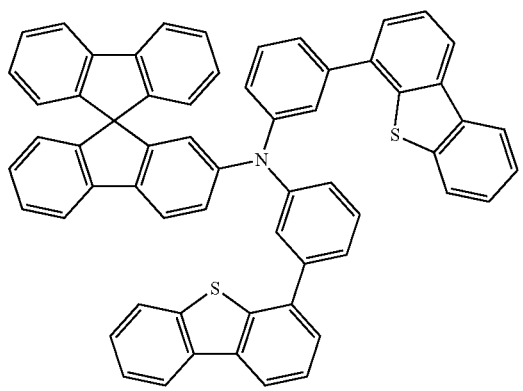
54
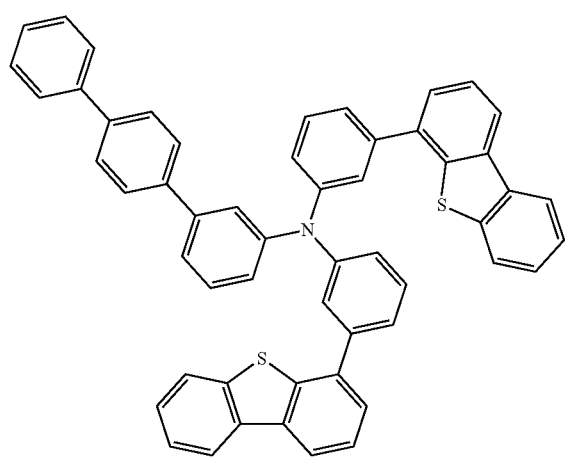
55
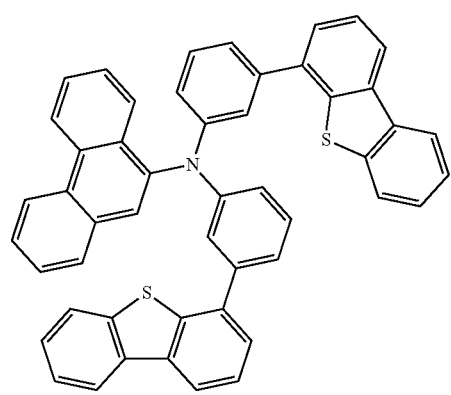
56
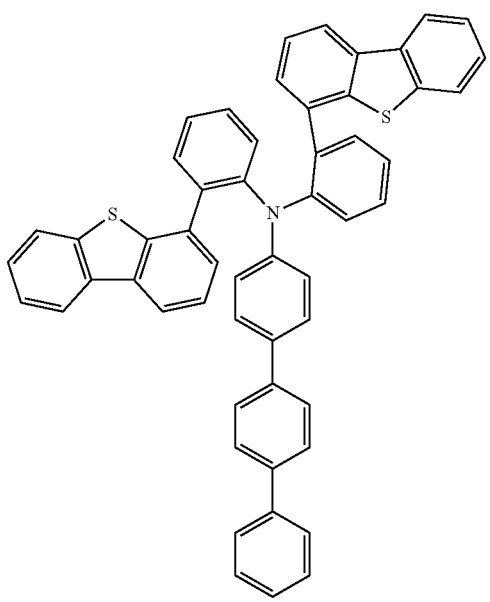
57
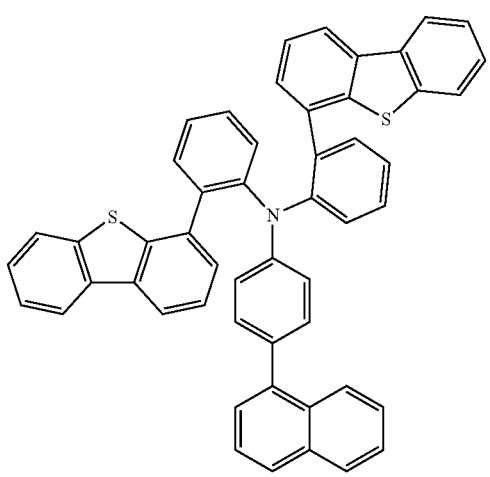
58
59

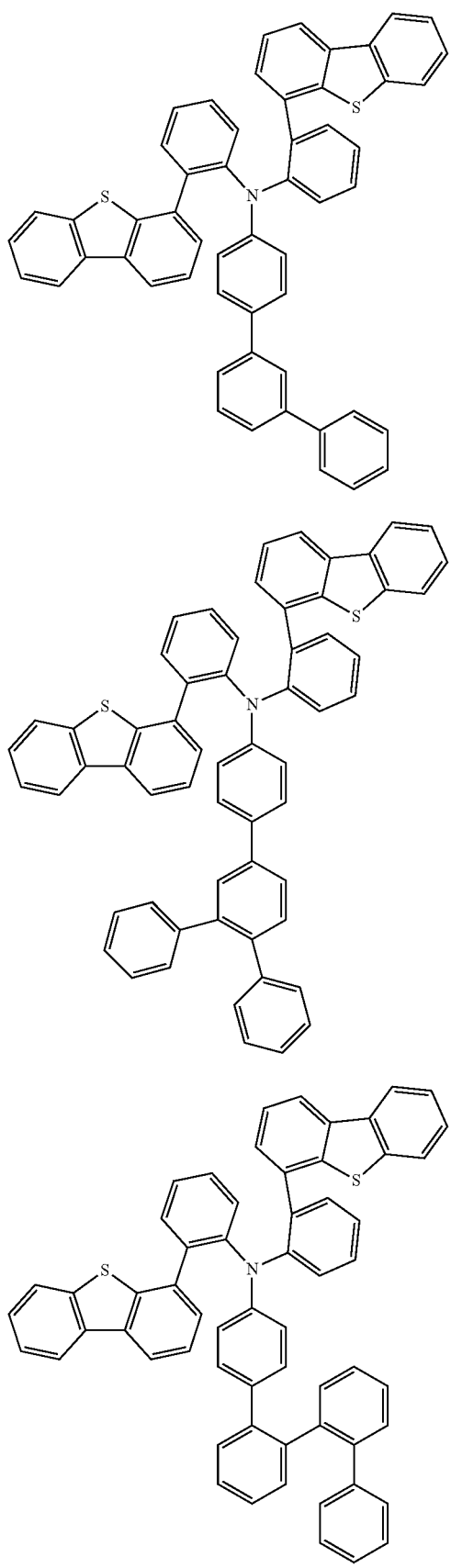

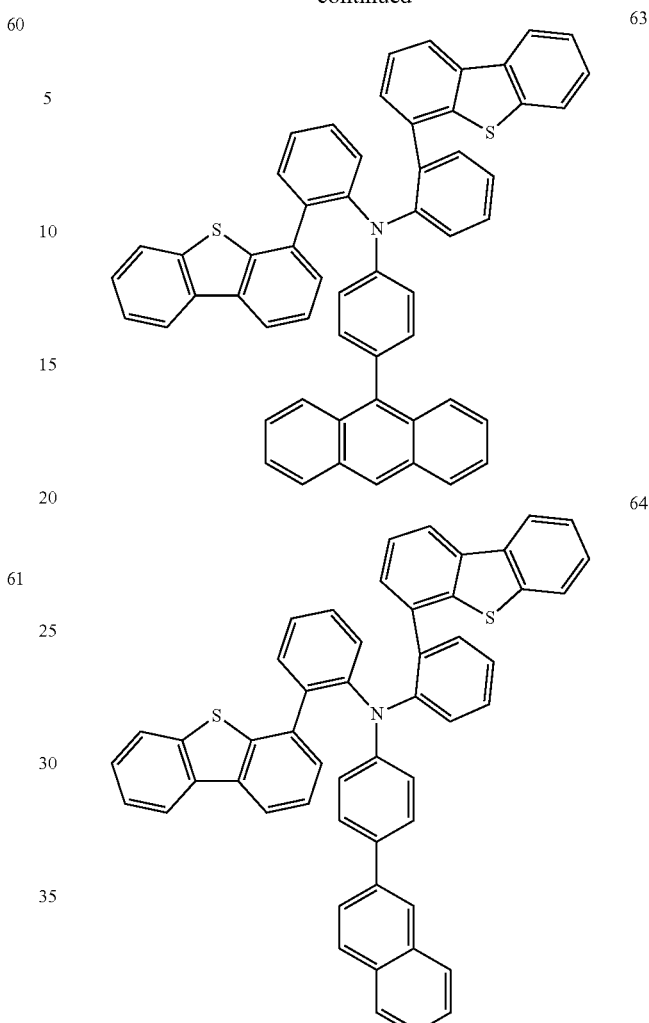

In another implementation of the present disclosure, there is provided an organic light-emitting device that includes a first electrode, a second electrode, and at least one organic material layer between the first and second electrodes, wherein the organic material layer contains the compound represented by the Chemical Formula 1:

Chemical Formula 1

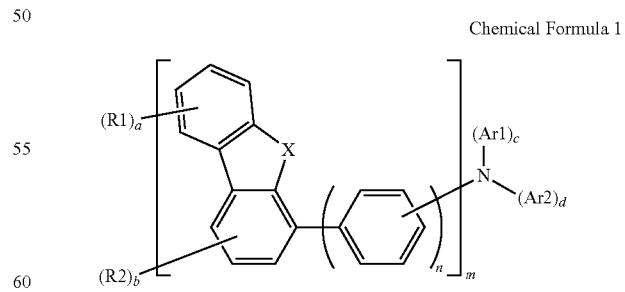

where, in the Chemical Formula 1,
X represents O or S,
each of R1 and R2 independently represents a substituent selected from the group consisting of an aryl group having 6 to 30 carbon atoms, a heteroaryl group having 5 to 30 carbon atoms, an alkyl group having 1 to 15 carbon atoms, a halogen atom, and a deuterium atom, a is an integer from 0 to 4, when a is 2 or more, R1s are the same as or different from each other, or adjacent R1s may be bonded to each other to form a ring, b is an integer from 0 to 3, when b is 2 or more, R2s are the same as or different from each other, or adjacent R2s may be bonded to each other to form a ring, n is 0 or 1, n=0 representing a direct bond, m is an integer from 1 to 3, each of c and d is an integer of 0 or 1, m, c, and d are selected such that when m is 1, c+d=2, when m is 2, c+d=1, and when m is 3, c+d=0, and each of Ar1 and Ar2 independently represents one selected from the group consisting of a substituted or unsubstituted aryl group having 6 to 30 carbon atoms, an alkyl group having 1 to 30 carbon atoms, an alkenyl group having 2 to 30 carbon atoms, an alkynyl group having 2 to 20 carbon atoms, an alkoxyl group having 1 to 30 carbon atoms, and an aryloxy group having 6 to 30 carbon atoms.

When the adjacent R1s are bonded to each other to form a ring, the ring may include a C5 to C30 alicyclic or C6 to C30 aromatic, single or polycyclic ring-based, saturated or unsaturated ring.

When the adjacent R2s are bonded to each other to form a ring, the ring may include a C5 to C30 alicyclic or C6 to C30 aromatic, single or polycyclic ring-based, saturated or unsaturated ring.

A detailed description of the compound represented by the Chemical Formula 1 is as described above.

The organic light-emitting device may include an organic material layer containing the compound represented by the Chemical Formula 1 as described above.

Specifically, the organic material layer containing the compound represented by the Chemical Formula 1 may include a hole transport layer or an auxiliary hole transport layer. In one implementation, the organic material layer includes a hole transport layer or an auxiliary hole transport layer containing the compound represented by the Chemical Formula 1.

In one implementation, the organic material layer may include at least two or more compounds represented by the Chemical Formula 1.

The organic material layer may include, in addition to the organic material layer containing the compound represented by Chemical Formula 1, at least one organic material layer selected from the group consisting of a hole injection layer, a hole transport layer, an auxiliary hole transport layer, a light-emitting layer, an auxiliary electron transport layer, an electron transport layer and an electron injection layer.

According to the present disclosure, the hole transport layer may be embodied as a single layer or a stack of a plurality of layers.

According to the present disclosure, the auxiliary hole transport layer may be embodied as a single layer or a stack of a plurality of layers.

FIG. 1 shows an organic light-emitting device according to one implementation of the present disclosure. In FIG. 1, the organic light-emitting device 100 includes an anode 110, a hole injection layer 131, a hole transport layer 132, a light emitting layer 133, an electron transport layer 134, and a cathode 120 in this order. The hole injection layer 131, the hole transport layer 132, the light emitting layer 133, and the electron transport layer 134 constitute the organic material layer 130.

The anode 110 feeds a hole into the light-emitting layer 133. The anode may contain a conductive material with a high work function to facilitate the feeding of the hole. When the organic light-emitting device is applied to a bottom emission organic light-emitting display device, the anode may be a transparent electrode made of a transparent conductive material. When the organic light-emitting device is applied to a top emission organic light-emitting display device, the anode may be a multilayer structure with a transparent electrode layer and a reflective layer made of a transparent conductive material.

The cathode 120 feeds electrons to the light-emitting layer 133. The cathode may contain a conductive material having a low work function to facilitate feeding of electrons. When the organic light-emitting device is applied to a bottom emission organic light-emitting display device, the cathode may be a reflective electrode made of metal. When the organic light-emitting device is applied to a top emission organic light-emitting display device, the cathode may be embodied as a transparent electrode made of a metal and having a small thickness.

Each of the light-emitting layers 133 may emit red R, green G and blue B light beams, and may be made of a phosphorescent material or a fluorescent material.

When each of the light-emitting layers 133 emits red light, and when each of the light-emitting layers 133 is made of a phosphorescent material, each of the light-emitting layers 133 may contain: a host material including CBP (carbazole biphenyl) or mCP(1,3-bis (carbazol-9-yl); and dopants doped into the host including at least one selected from the group consisting of PIQIr(acac)(bis(1-phenylisoquinoline) acetylacetonate iridium), PQIr(acac)(bis(1-phenylquinoline) acetylacetonate iridium), PQIr(tris(1-phenylquinoline) iridium), PtOEP(octaethylporphyrin platinum), and combinations thereof. Alternatively, when each of the light-emitting layers 133 emits red light, and when each of the light-emitting layers 133 is made of a fluorescent material, each of the light-emitting layers 133 may contain PBD:Eu (DBM)3(Phen) or perylene. However, the present disclosure is not limited thereto.

When each of the light-emitting layers 133 emits green light, and when each of the light-emitting layers 133 is made of a phosphorescent material, each of the light-emitting layers 133 may contain: a host material that includes CBP or mCP; and dopants doped into the host including Ir(ppy)3(fac tris(2-phenylpyridine)iridium). Alternatively, when each of the light-emitting layers 133 emits green light, and when each of the light-emitting layers 133 is made of a fluorescent material, each of the light-emitting layers 133 may contain Alq3(tris(8-hydroxyquinolino)aluminum). However, the present disclosure is not limited thereto.

When each of the light-emitting layers 133 emits blue light, and when each of the light-emitting layers 133 is made of a phosphorescent material, each of the light-emitting layers 133 may contain: a host material that includes CBP or mCP; and dopants doped into the host including (4,6-F2ppy) 2Irpic. Alternatively, when each of the light-emitting layers 133 emits blue light, and when each of the light-emitting layers 133 is made of a fluorescent material, each of the light-emitting layers 133 may contain at least one selected from the group consisting of spiro-DPVBi, spiro-6P, distyrylbenzene (DSB), distyrylarylene (DSA), PFO-based polymer and PPV-based polymer and combinations thereof, or may contain the compound of the Chemical Formula 1 as the blue fluorescent material. However, the present disclosure is not limited thereto.

Each of the hole injection layers 131 may facilitate the injection of holes.

Each of the hole injection layers 131 may be made of at least one selected from the group consisting of, for example, CuPc(cupper phthalocyanine), PEDOT(poly(3,4)-ethylenedioxythiophene), PANI(polyaniline), NPD(N,N-dinaphthyl-N,N'-diphenyl benzidine) and combinations thereof. However, the present disclosure is not limited thereto.

Each of the hole transport layers 132 may contain, as a hole transport material, a material electrochemically stabilized via cationization (i.e., by losing electrons). Alternatively, each of the hole transport layers 132 may contain a material that produces a stable radical cation as a hole transport material. Each of the hole transport layers 132 may contain a known hole transport material or the compound represented by the Chemical Formula 1. The detailed description of the compound represented by the Chemical Formula 1 is as described above.

Each of the hole transport layers 132 may further contain an additional hole transport material other than the compound represented by the Chemical Formula 1.

The known hole transport material or the additional hole transport material may contain aromatic amine to be easily cationized. In one example, the additional hole transport material may include at least one selected from the group consisting of NPD(N,N-dinaphthyl-N,N'-diphenylbenzidine), TPD(N,N'-bis-(3-methylphenyl)-N,N'-bis-(phenyl)-benzidine), spiro-TAD(2,2',7,7'-tetrakis(N,N-dimethylamino)-9,9-spirofluorene), MTDATA (4,4',4-Tris(N-3-methylphenyl-N-phenylamino)-triphenylamine) and combinations thereof. However, the present disclosure is not limited thereto.

An auxiliary hole transport layer may be positioned between each of the hole transport layers 132 and each of the light-emitting layers 133.

The auxiliary hole transport layer may contain the compound represented by the Chemical Formula 1, or may contain a known auxiliary hole transport material. The detailed description of the compound represented by the Chemical Formula 1 is as described above.

The auxiliary hole transport layer may further contain an additional auxiliary hole transport material other than the compound represented by the Chemical Formula 1.

Each of the known auxiliary hole transport material and the additional auxiliary hole transport material may include at least one selected from the group consisting of, for example, TCTA, tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, tri-p-tolylamine, 1,1-bis (4-(N,N'-di(ptolyl)amino)phenyl)cyclohexane (TAPC), MTDATA, mCP, mCBP, CuPc, N,N'-bis[4-[bis(3-methylphenyl)amino]phenyl]-N,N'-diphenyl-[1,1'-biphenyl]-4,4'-diamine (DNTPD), TDAPB, and combinations thereof. However, the present disclosure is not limited thereto.

The auxiliary electron transport layer may be positioned between each of the electron transport layers 134 and each of the light-emitting layers 133. The auxiliary electron transport layer may further contain an auxiliary electron transport material.

The auxiliary electron transport material may include at least one selected from the group consisting of, for example, oxadiazole, triazole, phenanthroline, benzoxazole, benzothiazole, benzimidazole, triazine, and combinations thereof. However, the present disclosure is not limited thereto.

Each of the electron transport layers 134 receive electrons from the cathode. Each of the electron transport layers 134 may transfer the supplied electrons to the light-emitting layer.

Each of the electron transport layers 134 may serve to facilitate the transport of electrons. Each of the electron transport layers 134 contains an electron transport material.

The electron transport material may be electrochemically stabilized by being anionic (i.e., by obtaining electrons). Alternatively, the electron transport material may produce the stable radical anion. Alternatively, the electron transport material may contain a heterocyclic ring to be easily anionized by heteroatoms.

In one example, the electron transport material may include at least one selected from the group consisting of, for example, PBD(2-(4-biphenylyl)-5-(4-tert-butylphenyl)-1,3,4oxadiazole), TAZ(3-(4-biphenyl)4-phenyl-5-tert-butylphenyl-1,2,4-triazole), spiro-PBD, TPBi(2,2',2-(1,3,5-benzinetriyl)-tris(1-phenyl-1-H-benzimidazole), oxadiazole, triazole, phenanthroline, benzoxazole, benzthiazole, and combinations thereof. However, the present disclosure is not limited thereto.

In one example, the electron transport material may include an organic metal compound such as an organic aluminum compound, or an organic lithium compound including at least one selected from the group consisting of, for example, Alq3(tris(8-hydroxyquinolino)aluminum), Liq (8-hydroxyquinolinolatolithium), BAlq(bis(2-methyl-8-quinolinolate)-4-(phenylphenolato)aluminium), and SAlq, etc. However, the present disclosure is not limited thereto.

Specifically, the organometallic compound may be an organic lithium compound.

More specifically, a ligand bound to the lithium of the organolithium compound may be a hydroxyquinoline based ligand.

The organic material layer may further include an electron injection layer.

The electron injection layer serves to facilitate the injection of electrons and contains an electron injection material. The electron injection material may include, but is not limited to, at least one selected from the group consisting of Alq3(tris(8-hydroxyquinolino)aluminum), PBD, TAZ, Spiro-PBD, BAlq, SAlq and combinations thereof. Alternatively, the electron injection layer may be made of a metal compound. The metal compound may include, but is not limited to, at least one selected from the group consisting of, for example, LiQ, LiF, NaF, KF, RbF, CsF, FrF, $BeF_2$, $MgF_2$, $CaF_2$, $SrF_2$, $BaF_2$ and $RaF_2$.

The organic material layer may further include at least one selected from the group consisting of the hole injection layer, the hole transport layer, the auxiliary hole transport layer, the light-emitting layer, the auxiliary electron transport layer, the electron transport layer and the electron injection layer. Each of the hole injection layer, hole transport layer, auxiliary hole transport layer, light-emitting layer, auxiliary electron transport layer, electron transport layer and electron injection layer may be embodied as a single layer or a stack of multiple layers.

The organic light-emitting device according to the present disclosure may be applied to organic light emitting display devices such as a mobile phone and TV. For example, FIG. 2 is a schematic cross-sectional view of an organic light emitting display device applicable to a mobile phone according to an exemplary embodiment of the present disclosure.

As shown in FIG. 2, the organic light-emitting display device 1000 may include a substrate 1100, an organic light-emitting device 3000, and an encapsulating layer 2200 covering the organic light-emitting device 3000.

On the substrate 1100, a drive thin-film transistor TFT, which is a drive device, and the organic light-emitting device 3000, which is connected to the drive thin-film transistor TFT, are positioned.

Although not shown, on the substrate 1100, a gate line and a data line, which define a pixel region, a power line extending parallel to and spaced from either the gate line or the data line, and a switching thin-film transistor connected to the gate line and data line are formed.

The driving thin-film transistor TFT is connected to the switching thin-film transistor, and includes an active layer 1520, a gate electrode 1720, a source electrode 1920 and a drain electrode 1940. A gate insulating film 1600 and an inter-layer insulating film 1800 are interposed therebetween. As shown in FIG. 2, the source electrode 1920 and the drain electrode 1940 are electrically connected to the active layer 1520 via a contact hole formed in the gate insulating film 1600 and the inter-layer insulating film 1800. The drain electrode 1940 is connected to a first electrode 3100 of the organic light-emitting device 3000.

A storage capacitor Cst is connected to a power line and one electrode of the switching thin-film transistor and includes a storage first electrode 1540, a storage second electrode 1740 and a storage third electrode 1960. As shown in FIG. 2, the gate insulating film 1600 and the inter-layer insulating film 1800 are interposed between the storage first electrode 1540 and the storage second electrode 1740, and between the storage second electrode 1740 and the storage third electrode 1960, respectively.

The substrate 1100 may be made of a flexible material such as polyimide, or may be made of rigid material such as glass.

A multi-layer structured buffer layer 1200 made of an insulating material such as silicon oxide or silicon nitride is formed on the entire surface over an entire face of the substrate 1100. The multi-layer structured buffer layer 1200 is embodied as a stack of multiple layers, for example, at least two layers or more.

A light-blocking layer 1300 is formed on the multi-layer structured buffer layer 1200, is made of molybdenum titanium alloy (MoTi) in one example. The light-blocking layer 1300 prevents light from being incident on the active layer 1520, thereby preventing the active layer 1520 from being deteriorated by light. An insulating film 1400 made of an insulating material such as silicon oxide or silicon nitride is formed on the light-blocking layer 1300 over an entire face of the substrate 1100. Alternatively, a contact hole may be formed to connect the active layer 1520 to the light-blocking layer 1300. In order to minimize change in a threshold voltage of the thin film transistor, which may occur when the light-blocking layer 1300 is in a floating state, the light-blocking layer 1300 may be electrically connected to the active layer 1520.

The active layer 1520 embodied as a semiconductor film is formed on the insulating film 1400. The semiconductor film may be made of an oxide semiconductor material, or a single crystal silicon. Alternatively, the active layer 1520 may be made of polycrystalline silicon. In this case, the active layer 1520 may be doped with impurities into both edges thereof.

The storage first electrode 1540 is formed together with the active layer 1520 on the insulating film 1400. In this connection, the storage first electrode 1540 may be made of polycrystalline silicon in the same manner as the active layer 1520. The storage first electrode 1540 made of polycrystalline silicon is doped with impurities to have conductance.

A gate insulating film 1600 is formed on the insulating film 1400 so that the active layer 1520 and the storage first electrode 1540 are covered with the gate insulating film 1600. The gate insulating film 1600 is formed over an entire face of the substrate 1100. The gate insulating film 1600, for example, may be made of silicon oxide.

A gate electrode 1720 and a storage second electrode 1740 may be formed together on the gate insulating film 1600. The gate electrode 1720 and a storage second electrode 1740 overlap the active layer 1520 and the storage first electrode 1540 respectively. Each of the gate electrode 1720 and the storage second electrode 1740 may be formed of a stack of double metal layers, a first layer made of Cu and a second layer made of MoTi alloy.

An inter-layer insulating film 1800 of insulating material is formed ono an entire face of the gate insulating film 1600 to cover the gate electrode 1720 and the storage second electrode 1740. The inter-layer insulating film 1800 may be made of an inorganic insulating material such as silicon oxide or silicon nitride, or made of an organic insulating material such benzocyclobutene or photo-acryl.

As shown in FIG. 2, the gate insulating film 1600 and the inter-layer insulating film 1800 have two active layer contact holes defined therein for exposing both sides of the active layer 1520. The two active layer contact holes are respectively located to be spaced from both sides of the gate electrode 1720.

On the inter-layer insulating film 1800, a source electrode 1920 and a drain electrode 1940 made of a conductive material such as a metal are formed. The source electrode 1920 and the drain electrode 1940 are disposed around the gate electrode 1720 and are spaced from each other. The source electrode 1920 and the drain electrode 1940 are electrically connected to both sides of the active layer 1520 via the two active layer contact holes as described above respectively. The source electrode 1920 is connected to the power line (not shown).

Further, on the inter-layer insulating film 1800, a storage third electrode 1960 defining the storage capacitor Cst and made of a conductive material such as a metal together is formed together with the source electrode 1920 and the drain electrode 1940.

The active layer 1520, the gate electrode 1720, the source electrode 1920, and the drain electrode 1940 constitute the drive thin-film transistor TFT. The drive thin-film transistor TFT has a coplanar structure in which the gate electrode 1720, the source electrode 1920 and the drain electrode 1940 are positioned above the active layer 1520.

Alternatively, the drive thin-film transistor TFT may have an inverted staggered structure where the gate electrode is positioned below the active layer, while the source and drain electrodes are positioned above the active layer. In this case, the active layer may be made of amorphous silicon. In one example, the switching thin-film transistor (not shown) may have substantially the same structure as the drive thin-film transistor TFT.

A planarization layer 2000 having a drain contact-hole defined therein for exposing the drain electrode 1940 of the driving thin-film transistor TFT is formed to cover the drive thin-film transistor TFT and the storage capacitor Cst. The planarization layer 2000 may be made of an inorganic insulating material or an organic insulating material.

A first electrode 3100 is formed on the planarization layer 2000 such that the first electrode 3100 is connected to the drain electrode 1940 of the drive thin-film transistor TFT via the drain contact-hole defined in the planarization layer 2000. Accordingly, the active layer 1520 of the drive thin-film transistor TFT is electrically connected to the first electrode 3100.

The first electrode 3100 may act as an anode, and may be made of a conductive material having a relatively large work function value. For example, the first electrode 3100 may be made of transparent conductive material such as ITO. IZO or ZnO.

In one example, when the organic light-emitting display device 1000 is of a top emission type, a reflective electrode or reflective layer may be further formed below the first electrode 3100. For example, the reflective electrode or reflective layer may be made of any one of aluminum (Al), silver (Ag), nickel (Ni), aluminum-palladium-copper (APC alloy).

A bank layer 2100 is formed on the planarization layer 2000 to define each pixel region. The bank layer 2100 may allow a bank hole corresponding to each pixel region to be defined to partially expose the first electrode 3100.

An organic material layer 3300 is formed on the bank layer 2100 and a portion of the first electrode 3100 exposed by the bank hole. A portion of the organic material layer 3300 that is in contact with the first electrode 3100 corresponds to each pixel region, and more specifically to a light-emission region.

A second electrode 3200 is formed on the organic material layer 3300 over an entire face of the substrate 1100. The second electrode 3200 is positioned on an entirety of the expression region and may be made of a conductive material having a relatively small work function value and thus may act as a cathode. For example, the second electrode 3200 may be made of any one of aluminum Al, magnesium Mg, and aluminum-magnesium alloy AlMg.

The first electrode 3100, organic material layer 3300 and second electrode 3200 constitute the organic light-emitting device 3000.

The encapsulating layer 2200 is formed on the organic light-emitting device 3000 to prevent external moisture from penetrating the organic light-emitting device 3000.

The encapsulating layer 2200 may have, but is not limited to, a triple layer structure (not shown) sequentially composed of a first inorganic layer, and an organic layer, and a second inorganic layer.

On top of the encapsulating layer 2200, a barrier layer 2300 may be formed to more effectively prevent external moisture or oxygen from invading the organic light-emitting device 3000.

The barrier layer 2300 may be manufactured in a form of a film and adhered to the encapsulating layer 2200 via an adhesive.

Hereinafter, Examples and Comparative examples will be set forth. The Examples may be only an example of the present disclosure. Thus, the present disclosure is not limited to the Examples.

EXAMPLES

Hereinafter, compounds in accordance with Examples and Comparative Examples were synthesized as follows.

Synthesis Example 1

Compound A

Production of Compound A
Reaction Formula 1

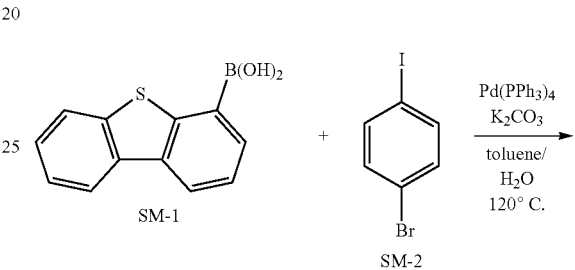

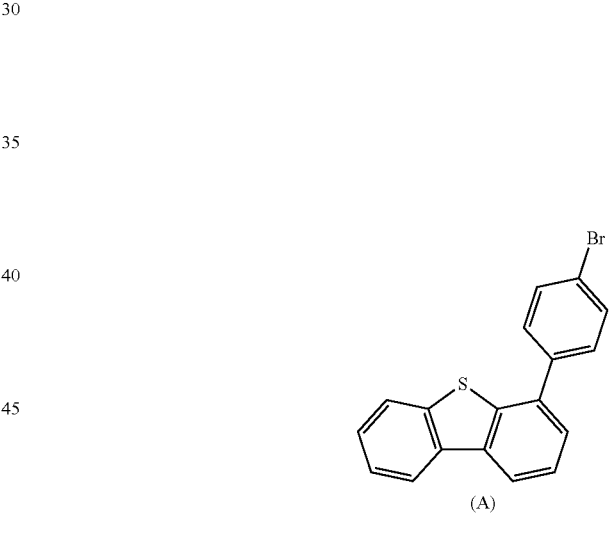

A compound SM (starting material)-1 (4.6 g, 20 mmol), SM (starting material)-2 (5.7 g, 20 mmol), Pd(PPh$_3$)$_4$ (1.2 g, 1 mmol), and K$_2$CO$_3$ (8.3 g, 60 mmol) were dissolved into a mixed solution of toluene 200 ml and water 50 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound A (6.5 g, yield: 96%).

Synthesis Example 2

Compound B

Production of Compound B
Reaction Formula 2

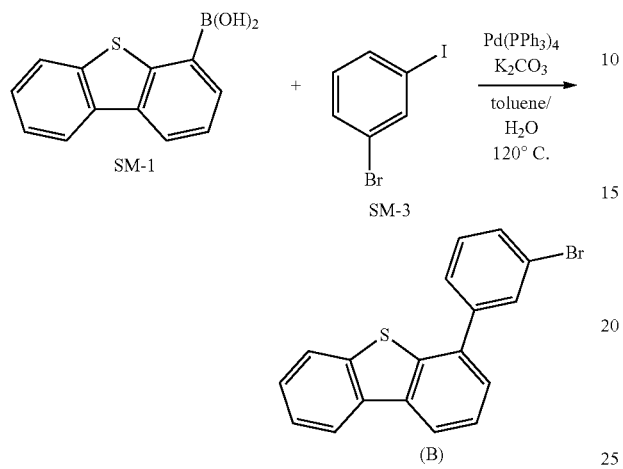

(B)

A compound SM (starting material)-1 (4.6 g, 20 mmol), SM (starting material)-3 (5.7 g, 20 mmol), Pd(PPh$_3$)$_4$ (1.2 g, 1 mmol), and K$_2$CO$_3$ (8.3 g, 60 mmol) were dissolved into a mixed solution of toluene 200 ml and water 50 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound B (6.6 g, yield: 97%).

Synthesis Example 3

Compound C

Production of Compound C
Reaction Formula 3

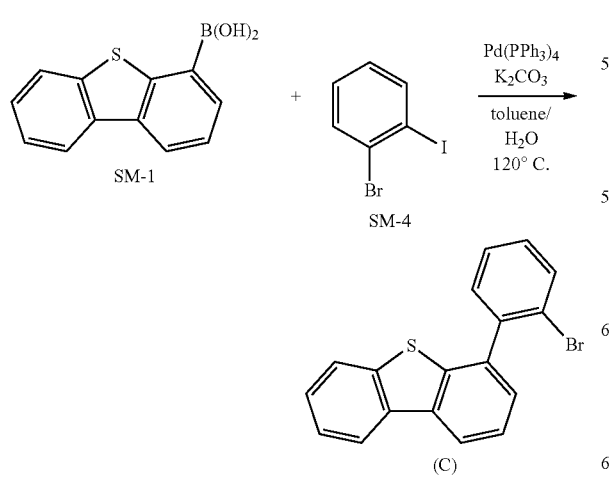

(C)

A compound SM (starting material)-1 (4.6 g, 20 mmol), SM (starting material)-4 (5.7 g, 20 mmol), Pd(PPh$_3$)$_4$ (1.2 g, 1 mmol), and K$_2$CO$_3$ (8.3 g, 60 mmol) were dissolved into a mixed solution of toluene 200 ml and water 50 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound C (6.0 g, yield: 89%).

Synthesis Example 4

Compound 2

Production of Compound 2
Reaction Formula 4

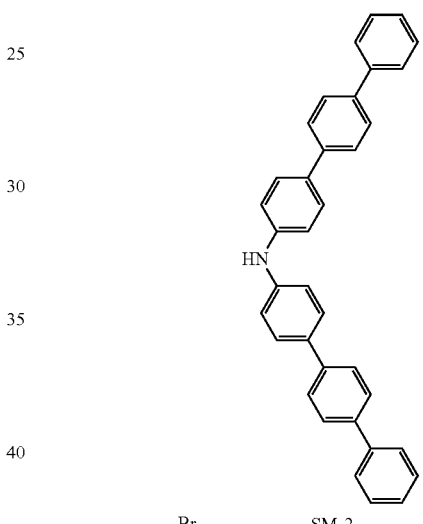

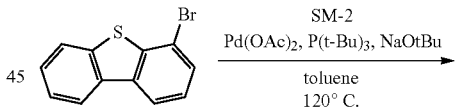

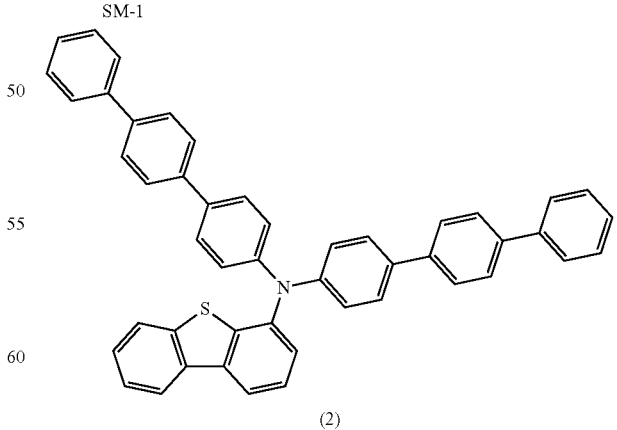

(2)

A compound SM (starting material)-1 (5.3 g, 20 mmol), SM (starting material)-2 (9.5 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled away under a reduced pressure and removed from the organic layer and then was subjected to column purification, thereby to obtain the compound 2 (12.6 g, yield: 96%).

Synthesis Example 5

Compound 14

Production of Compound 14
Reaction Formula 5

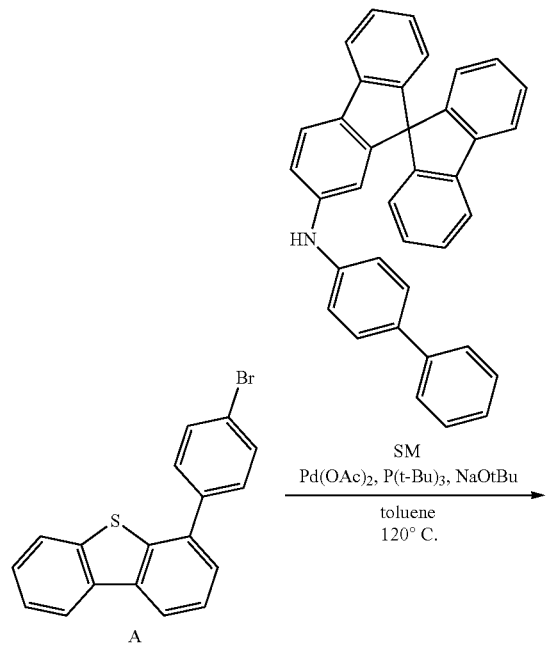

The compound A (6.8 g, 20 mmol), SM (starting material) (7.2 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 14 (13.4 g, yield: 90%).

Synthesis Example 6

Compound 18

Production of Compound 18
Reaction Formula 6

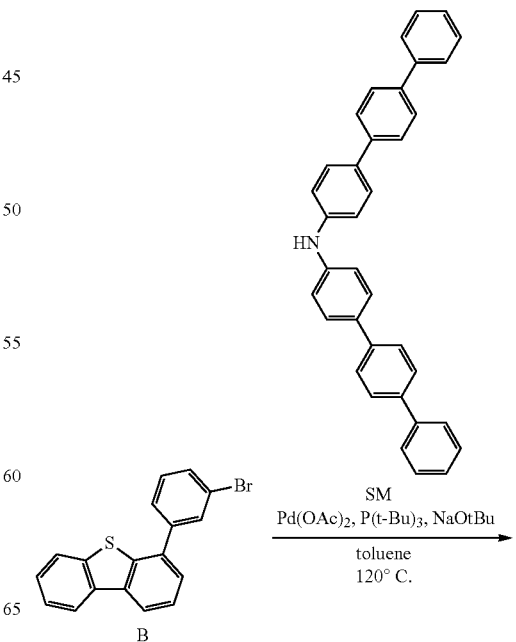

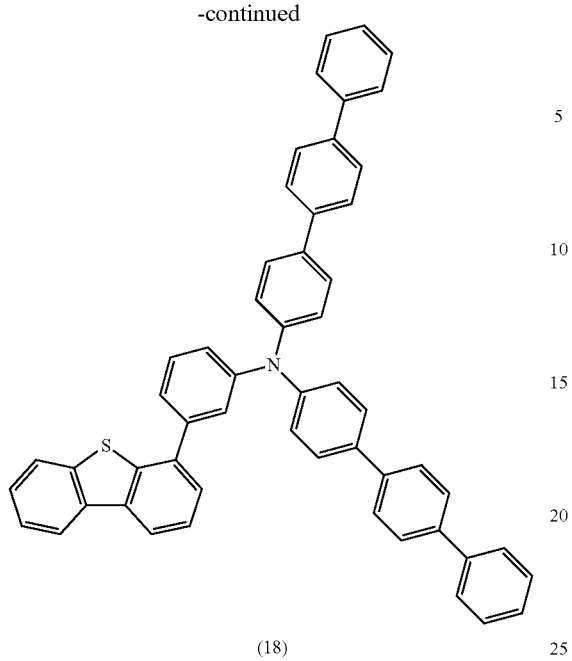

(18)

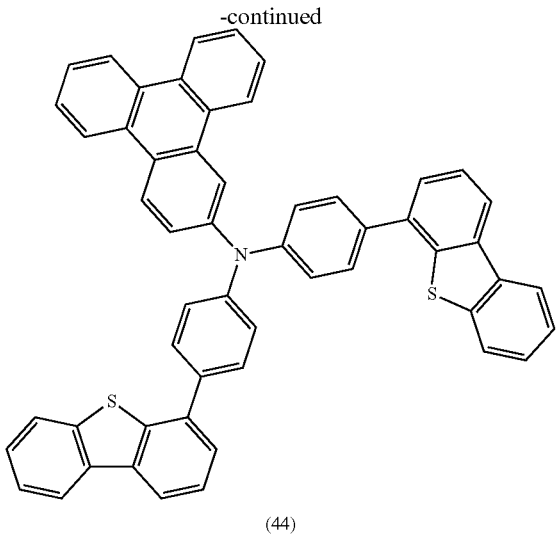

(44)

The compound B (6.8 g, 20 mmol), SM (starting material) (9.5 g, 20 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 18 (13.5 g, yield: 92%).

Synthesis Example 7

Compound 44

Production of Compound 44
Reaction Formula 7

The compound A (6.8 g, 20 mmol), SM (starting material) (2.4 g, 10 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 44 (6.7 g, yield: 88%).

Synthesis Example 8

Compound 57

Production of Compound 57
Reaction Formula 8

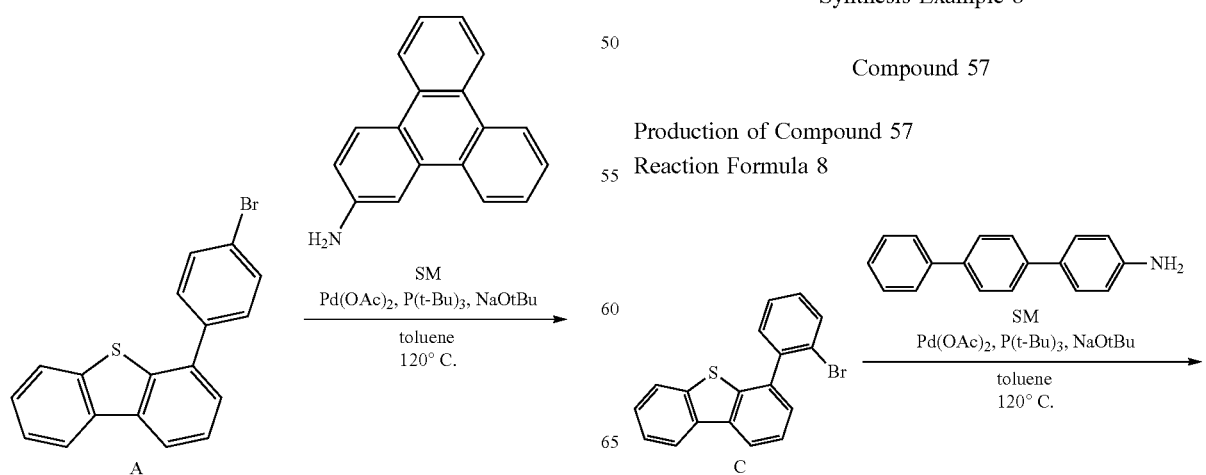

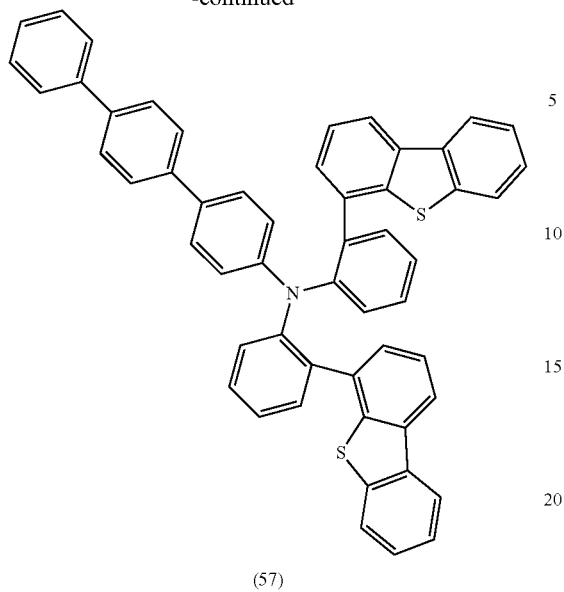

(57)

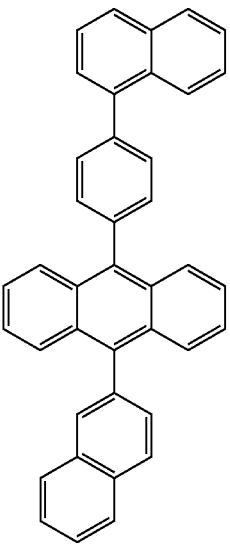

BH-1

The compound C (6.8 g, 20 mmol), SM (starting material) (2.5 g, 10 mmol), Pd(OAc)$_2$ (0.45 g, 2 mmol), P(t-Bu)$_3$ (0.81 g, 4 mmol), and NaOtBu (7.7 g, 80 mmol) were dissolved into toluene 200 ml in a 500 ml round bottom flask under a nitrogen atmosphere to form a mixture. Then, the mixture was heated and stirred while being refluxed for 12 hours. An organic layer was extracted with chloroform and washed with water. Water was removed from the organic layer with anhydrous magnesium sulfate and the organic layer was filtered. Then, an organic solvent was distilled under a reduced pressure and was removed from the organic layer and was subjected to column purification, thereby to obtain the compound 57 (6.7 g, yield: 88%).

Production of Organic Light-Emitting Device 1
Compound Used in Organic Light-Emitting Device 1

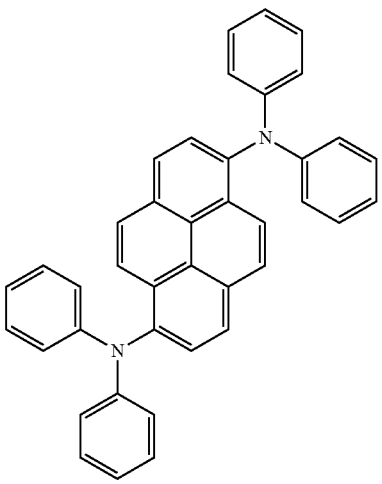

BD-1

HI-1

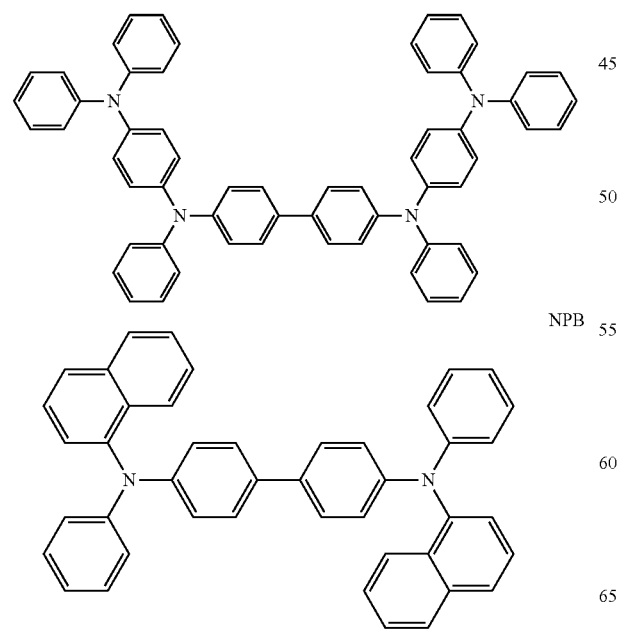

NPB

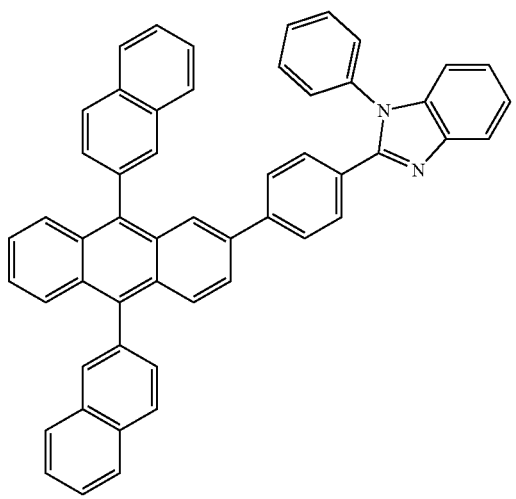

ET-1

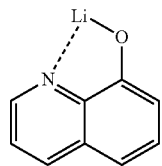

Example 1

After cleaning a glass substrate having an ITO (indium tin oxide) thin film coated thereon to a thickness of 1,000 Å, the substrate was ultrasonically washed with a solvent such as isopropyl alcohol, acetone, or methanol and dried. Then, HI-1 as a hole injection material was deposited to a thickness of 60 nm on the ITO transparent electrode via thermal vacuum deposition. Then, the Compound 2 as a hole transport material was thermally vacuum deposited to 80 nm thickness on the hole injection material. Subsequently, BH-1 and BD-1 was used as a host material and a dopant material (5 wt %) in a light-emitting layer respectively. Thus, the host material was thermally vacuum-deposited to a thickness of 30 nm on the hole transport material while the dopants were doped into the host material, thus form the light-emitting layer.

Then, an ET-1: Liq (1:1) compound was thermally vacuum deposited at 30 nm thickness as each of electron transport layer material and electron injection layer material on the light-emitting layer. Then, depositing aluminum as cathode material at a thickness of 100 nm on the electron injection layer resulted in an organic light-emitting device 1.

Examples 2 to 14

Organic light-emitting devices 1 were fabricated in the same manner as in Example 1 except that compounds shown in Table 1 were used in place of the compound 2 in the Example 1.

Comparative Example 1

An organic light-emitting device 1 was fabricated in the same manner as in Example 1 except that NPB compound was used instead of the compound 2 in the Example 1.

The organic light-emitting devices produced in Examples 1 to 14 and Comparative Example 1 were analyzed in terms of optical characteristic of the device at a constant current of 10 mA/cm². The organic light-emitting devices produced in Examples 1 to 14 and Comparative Example 1 were analyzed in terms of a lifespan under a driving condition of 20 mA/cm². Results thereof are shown in Table 1 below.

TABLE 1

| Examples | Hole transport material | Drive voltage (V) | mA/cm² | Cd/A | 1m/W | CIEx | CIEy | LT95 (hrs) |
|---|---|---|---|---|---|---|---|---|
| Comparative Example 1 | NPB | 4.52 | 100% | 100% | 100% | 0.141 | 0.110 | 100% |
| Example 1 | Compound 2 | 4.03 | 110% | 108% | 103% | 0.141 | 0.110 | 128% |
| Example 2 | Compound 3 | 4.05 | 111% | 108% | 105% | 0.141 | 0.111 | 125% |
| Example 3 | Compound 4 | 4.06 | 109% | 106% | 106% | 0.141 | 0.110 | 122% |
| Example 4 | Compound 14 | 4.08 | 109% | 107% | 106% | 0.140 | 0.111 | 134% |
| Example 5 | Compound 15 | 4.09 | 108% | 106% | 105% | 0.141 | 0.110 | 137% |
| Example 6 | Compound 18 | 4.16 | 114% | 110% | 111% | 0.139 | 0.110 | 138% |
| Example 7 | Compound 22 | 4.19 | 116% | 111% | 110% | 0.140 | 0.111 | 135% |
| Example 8 | Compound 24 | 4.17 | 114% | 112% | 109% | 0.141 | 0.110 | 137% |
| Example 9 | Compound 44 | 4.21 | 122% | 119% | 118% | 0.141 | 0.110 | 146% |
| Example 10 | Compound 45 | 4.20 | 120% | 116% | 115% | 0.141 | 0.111 | 142% |
| Example 11 | Compound 46 | 4.19 | 125% | 120% | 119% | 0.141 | 0.110 | 144% |
| Example 12 | Compound 57 | 4.38 | 128% | 122% | 120% | 0.141 | 0.111 | 152% |
| Example 13 | Compound 58 | 4.33 | 126% | 125% | 122% | 0.141 | 0.110 | 149% |
| Example 14 | Compound 59 | 4.30 | 122% | 121% | 120% | 0.141 | 0.111 | 151% |

As described above, the present disclosure is described with reference to the drawings. However, the present disclosure is not limited by the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

What is claimed is:

1. An organic light-emitting device comprising:
   a first electrode;
   a second electrode; and
   at least one organic material layer between the first and second electrodes,
   wherein the at least one organic material layer includes at least one layer selected from the group consisting of a hole transport layer, an auxiliary hole transport layer and a light-emitting layer, and
   wherein the at least one layer comprises at least two types of a compound represented by one of the following Chemical Formula 2, Chemical Formula 3, Chemical Formula 4, and Chemical Formula 5:

Chemical Formula 2

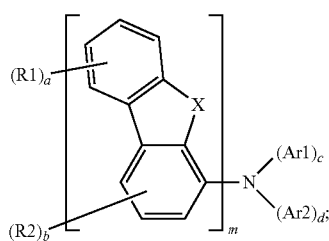

Chemical Formula 3

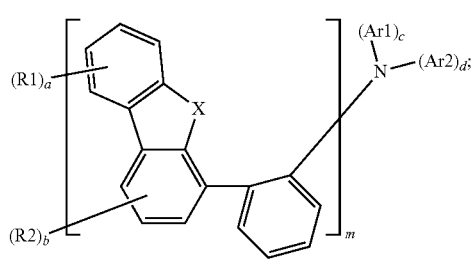

Chemical Formula 4

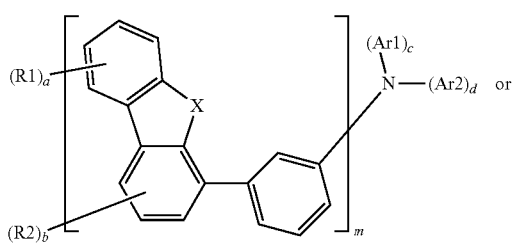

Chemical Formula 5

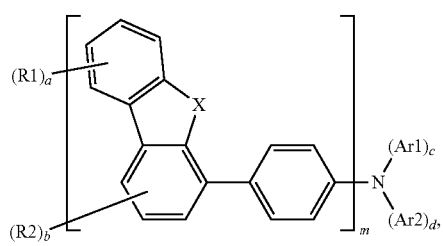

wherein:
X represents O or S,
each of R1 and R2 independently represents an aryl group having 6 to 30 carbon atoms, a heteroaryl group having 5 to 30 carbon atoms, an alkyl group having 1 to 15 carbon atoms, a halogen atom, or a deuterium atom,
each of Ar1 and Ar2 independently represents a substituted or unsubstituted aryl group having 6 to 30 carbon atoms, an alkyl group having 1 to 30 carbon atoms, an alkenyl group having 2 to 30 carbon atoms, an alkynyl group having 2 to 20 carbon atoms, an alkoxyl group having 1 to 30 carbon atoms, or an aryloxy group having 6 to 30 carbon atoms a is an integer from 0 to 4, provided that when a is 2 or more, the corresponding R1 is the same as or different from each other, or adjacent corresponding R1s are bonded to each other to form a ring, b is an integer from 0 to 3, provided that when b is 2 or more, the corresponding R2 is the same as or different from each other, or adjacent corresponding R2s are bonded to each other to form a ring, m is an integer from 1 to 3, each of c and d is independently an integer of 0 or 1, and m, c and d are selected such that when m is 1, c+d=2, when m is 2, c+d=1, and when m is 3, c+d=0.

2. The compound of claim 1, wherein each of Ar1 and Ar2 of the Chemical Formula 2 is independently selected from:

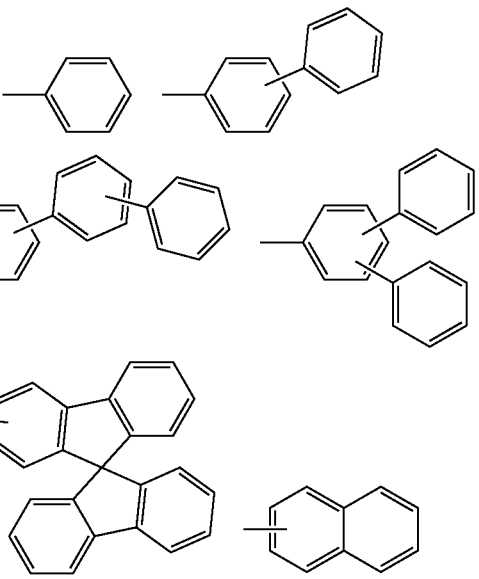

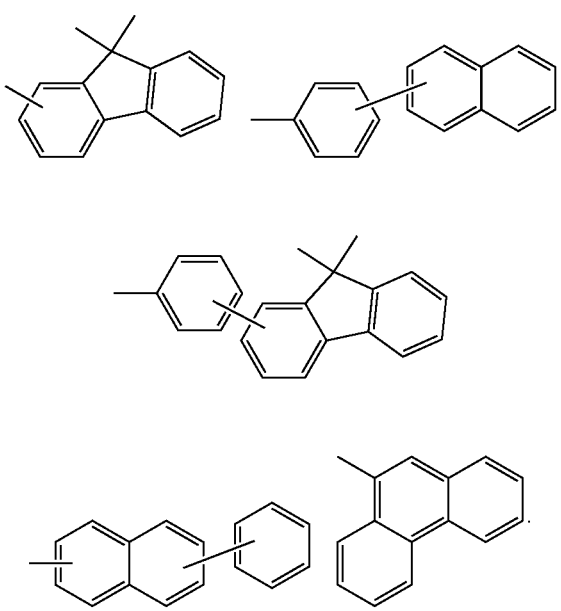

3. The compound of claim 1, wherein the compound has one of the following structures:
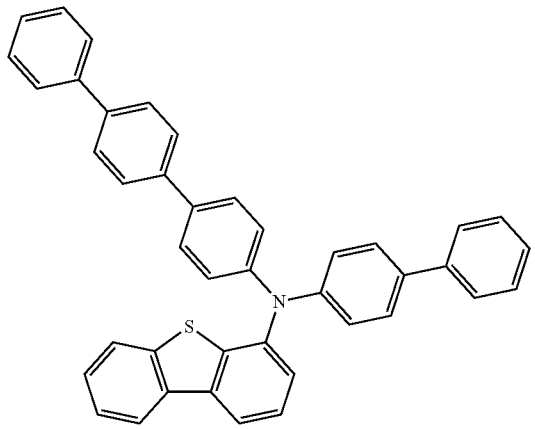
1
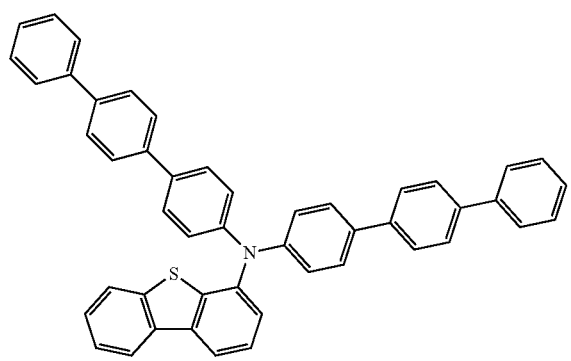
2
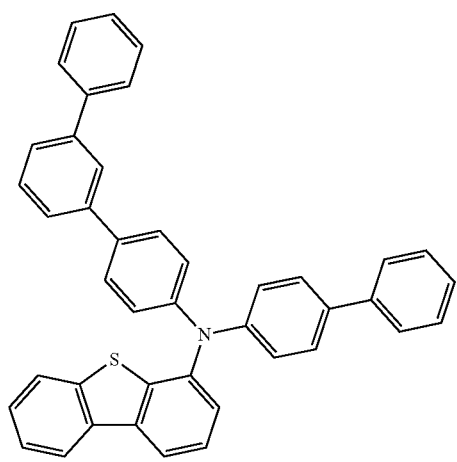
3
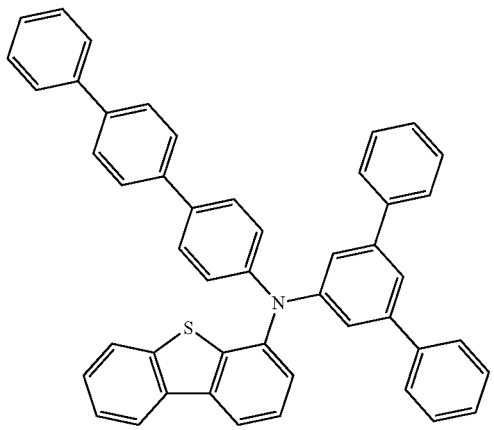
4
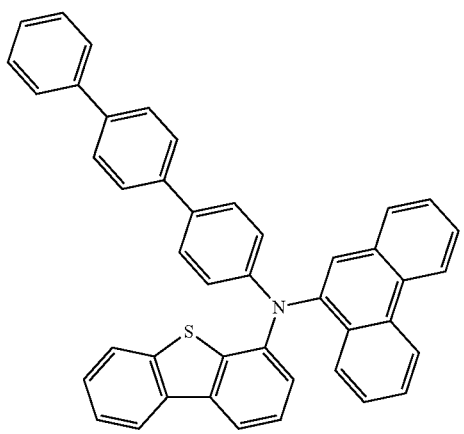
5
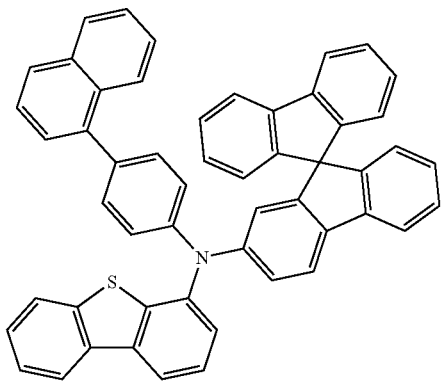
6

51
-continued
7
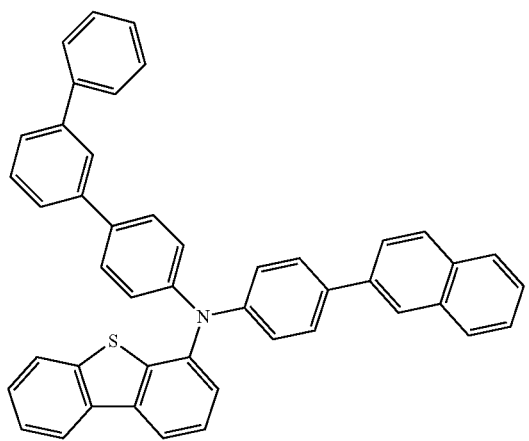
8
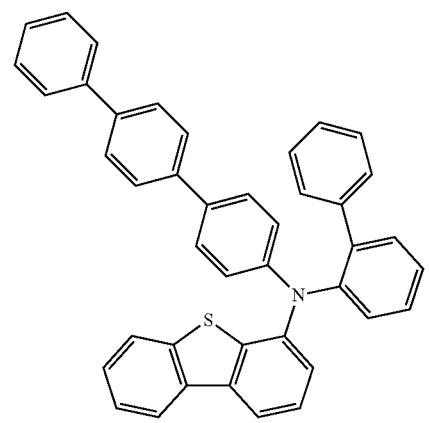
9
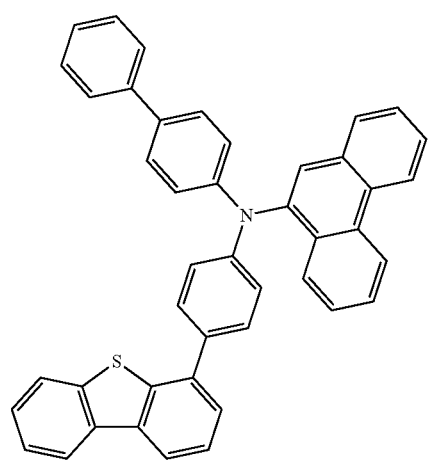
52
-continued
10
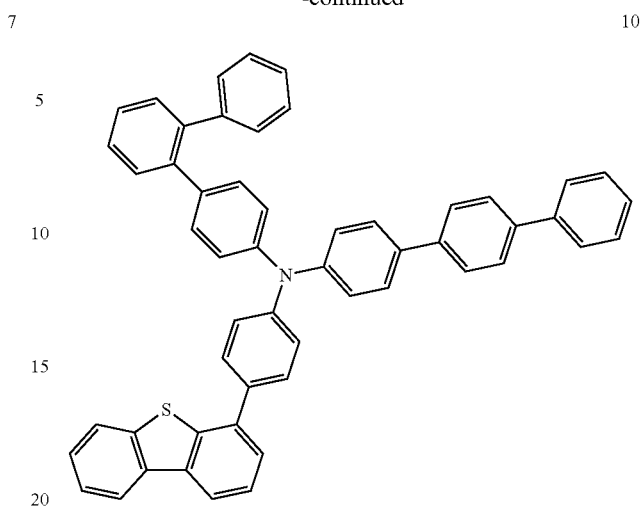
11
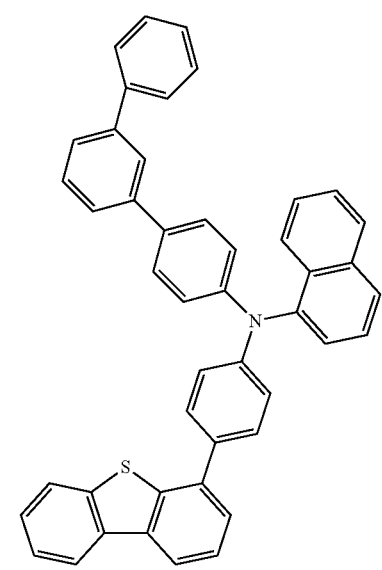
12
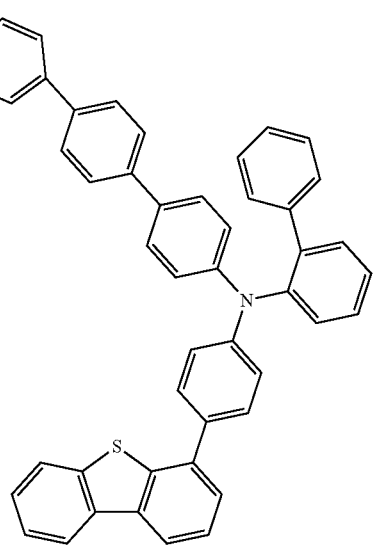

13
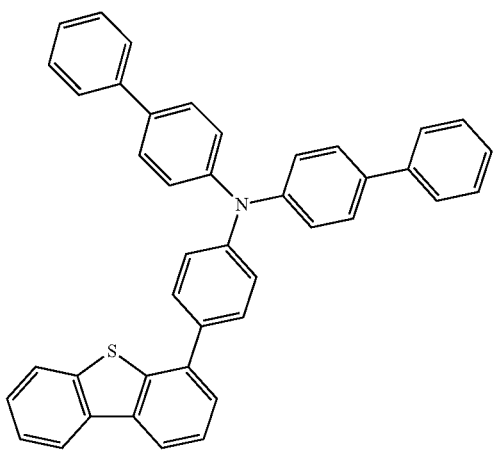
14
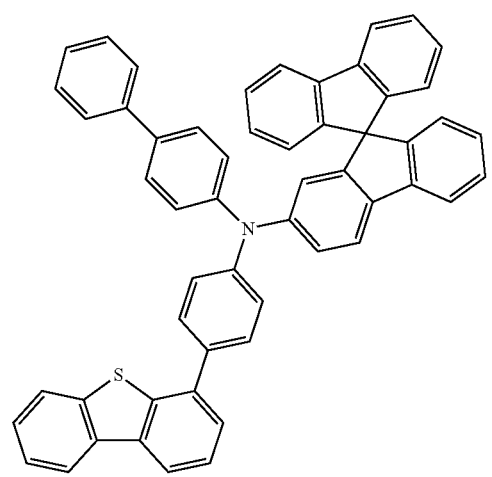
15
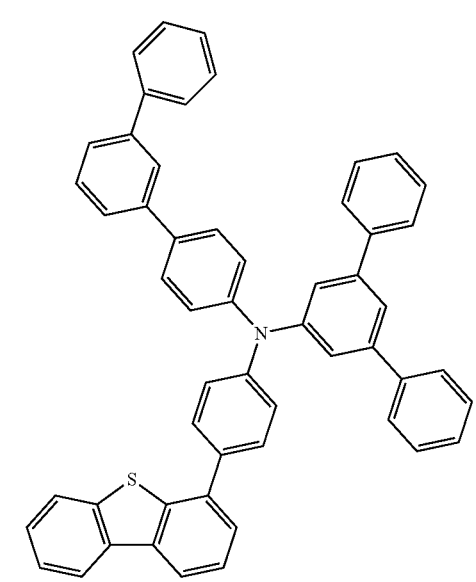
16
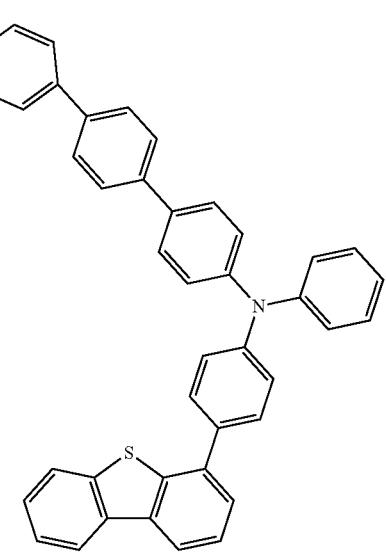
17
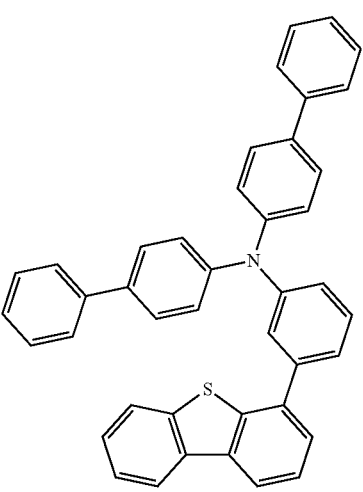
18
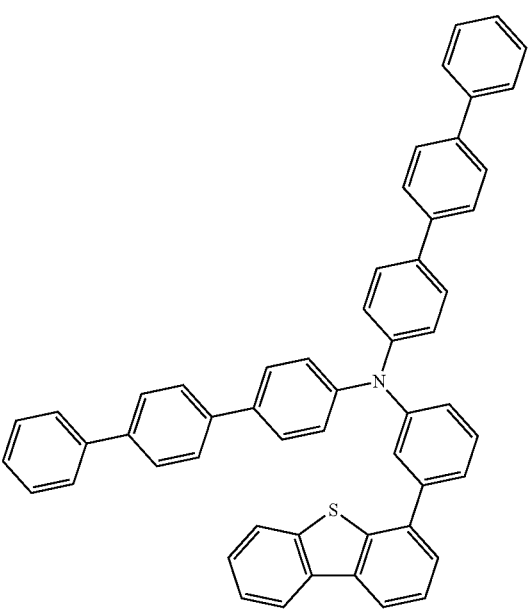

19
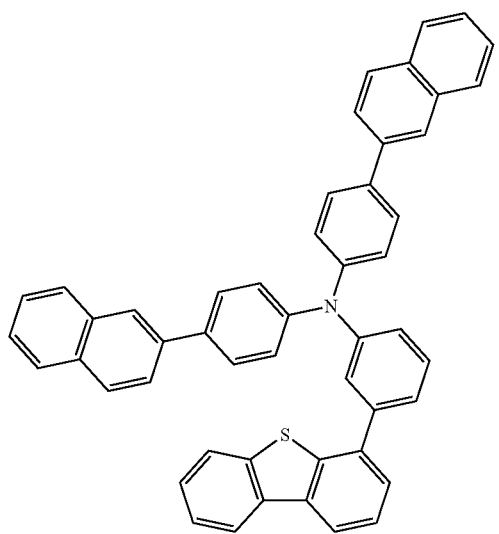
20
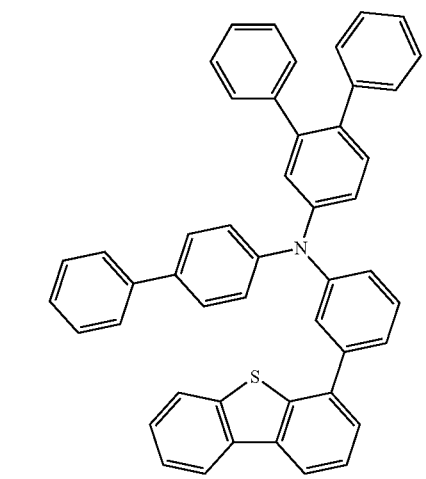
21
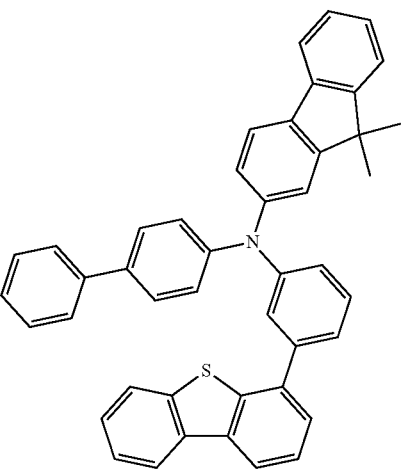
22
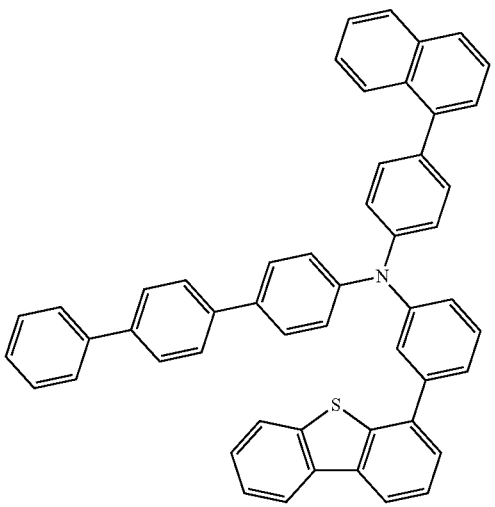
23
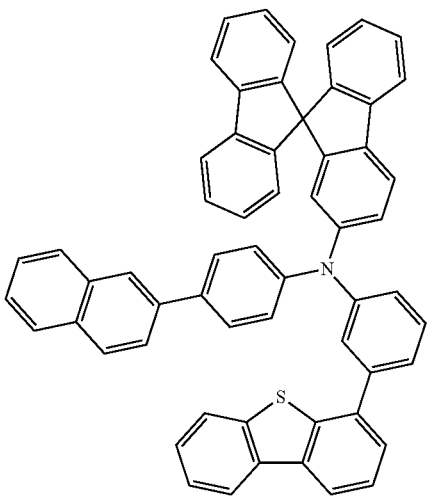
24
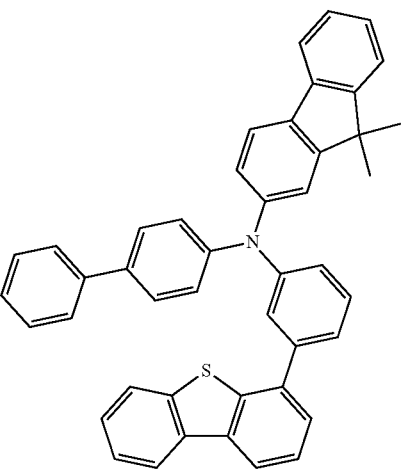

25
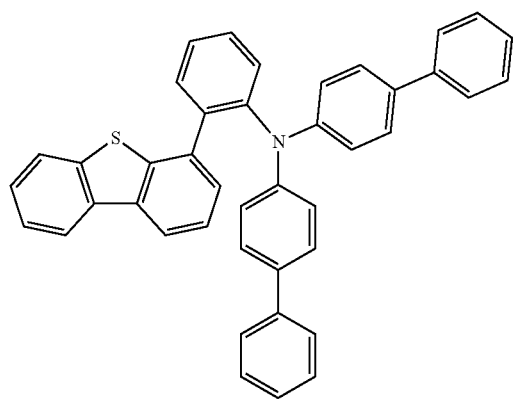
28
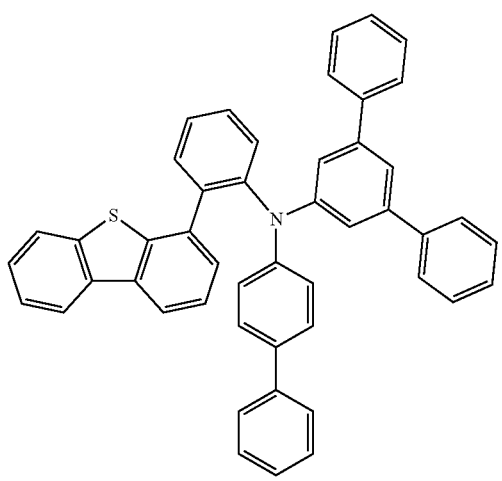
26
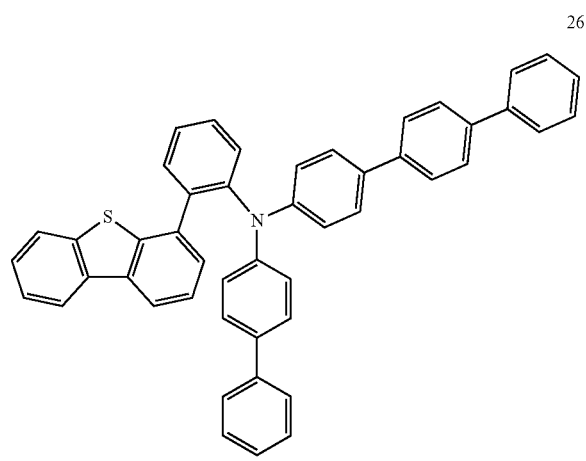
29
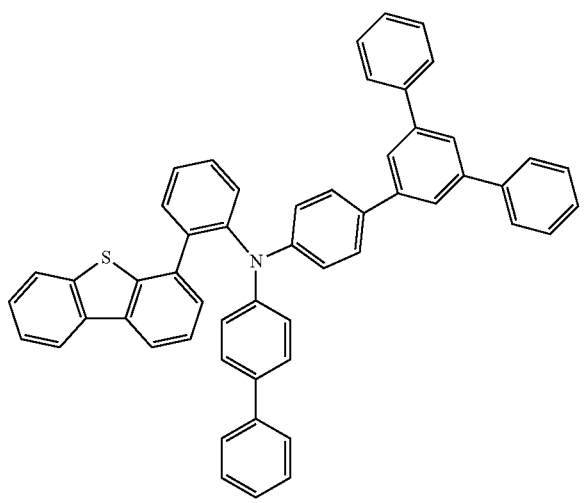
27
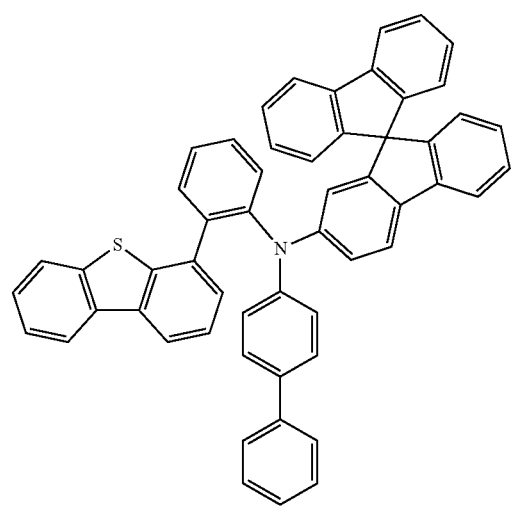
30
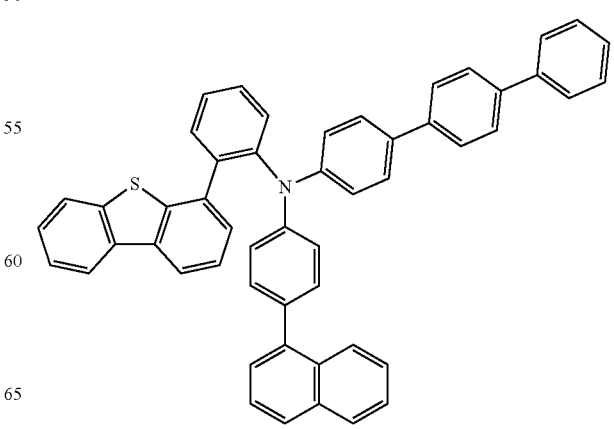

31
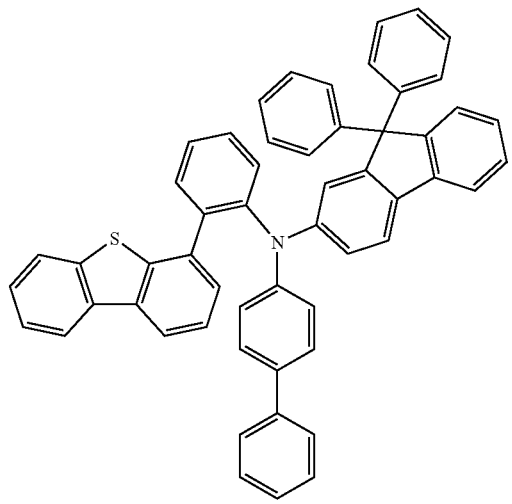
32
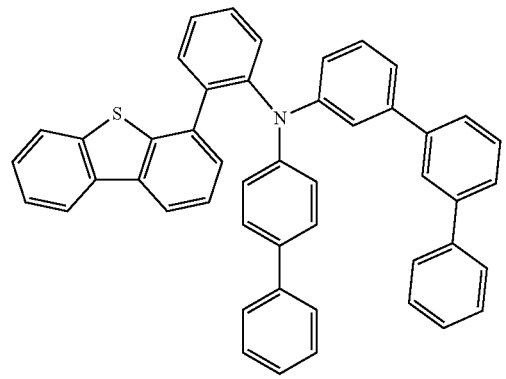
33
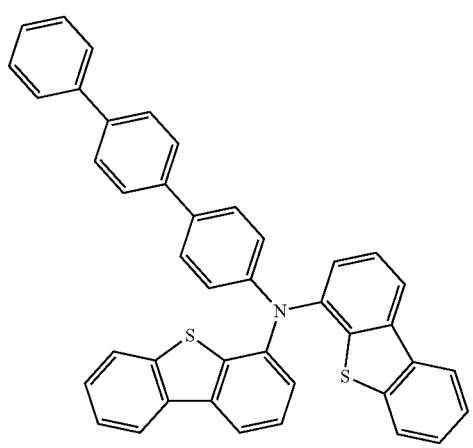
34
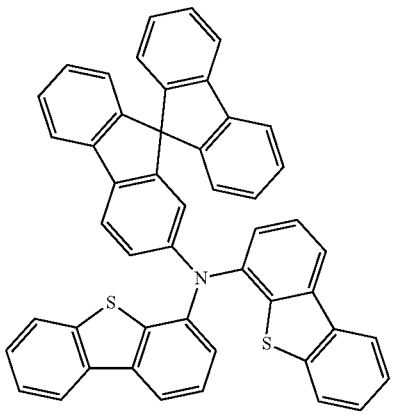
35
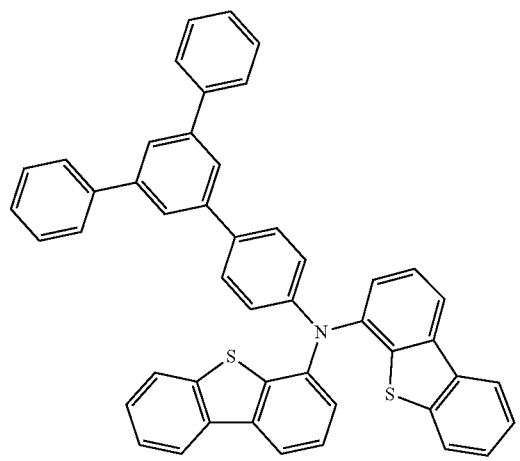
36
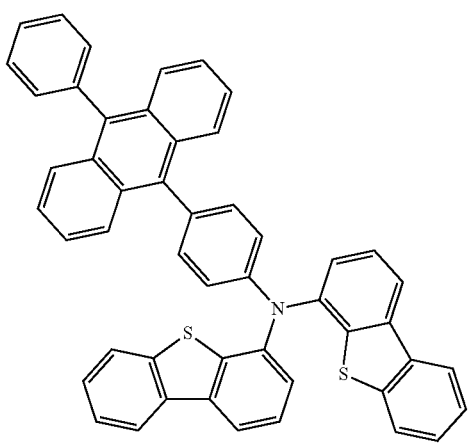

37
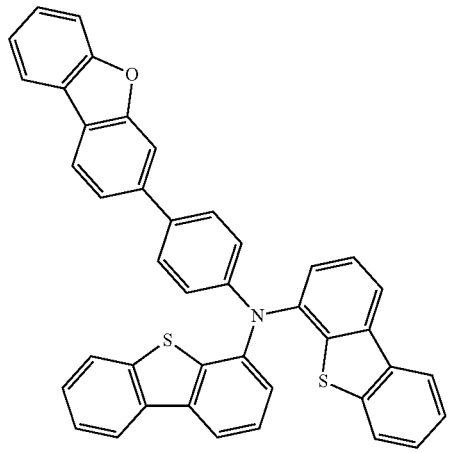
38
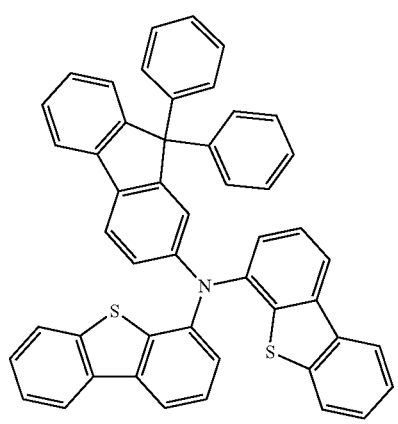
39
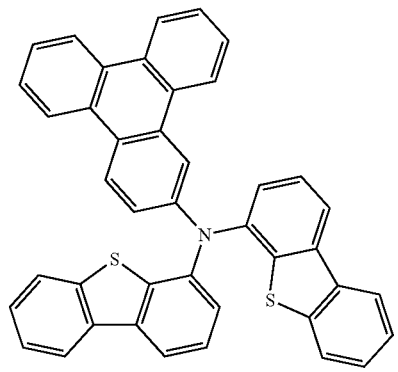
40
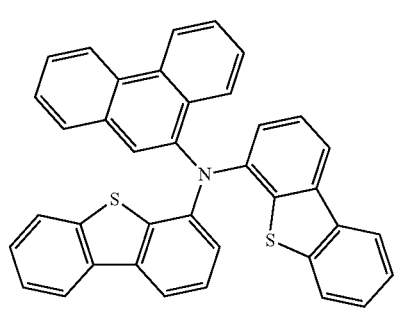
41
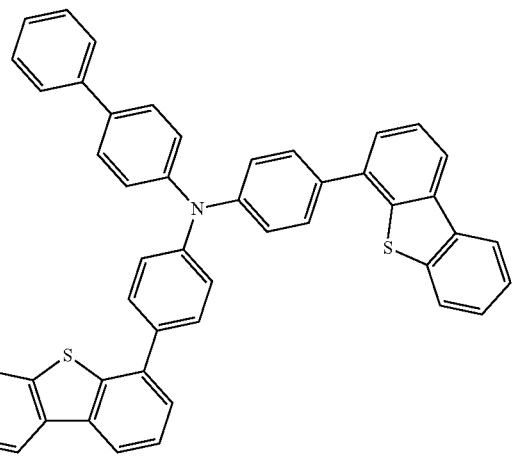
42
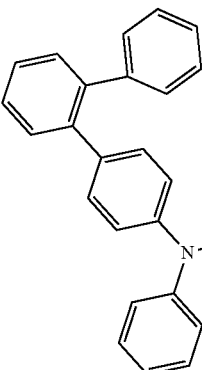
43
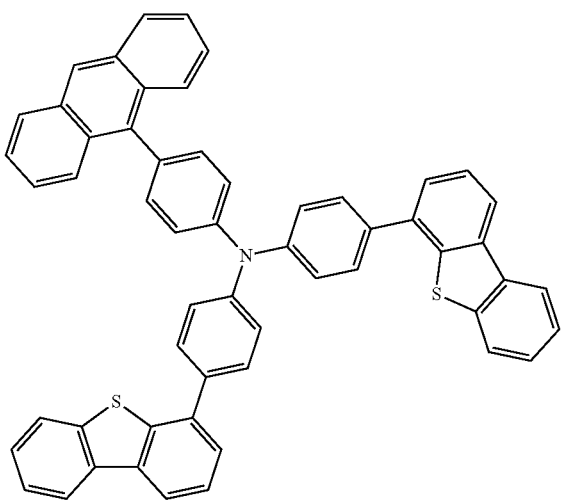

44
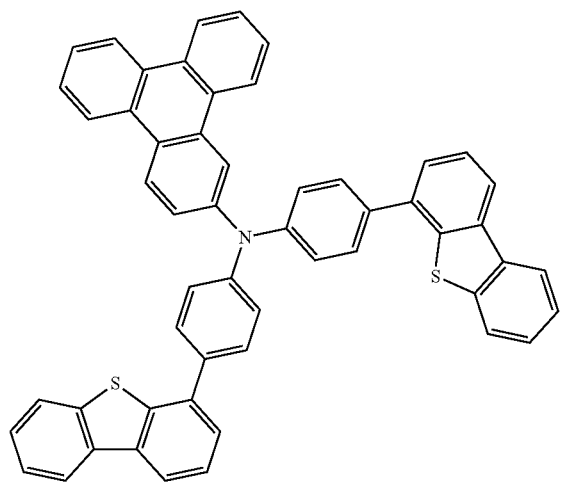
45
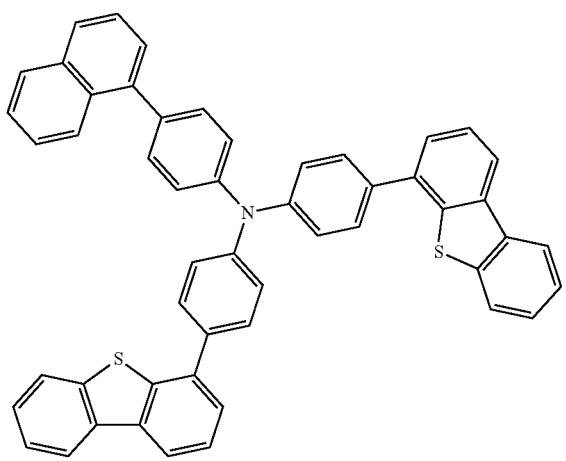
46
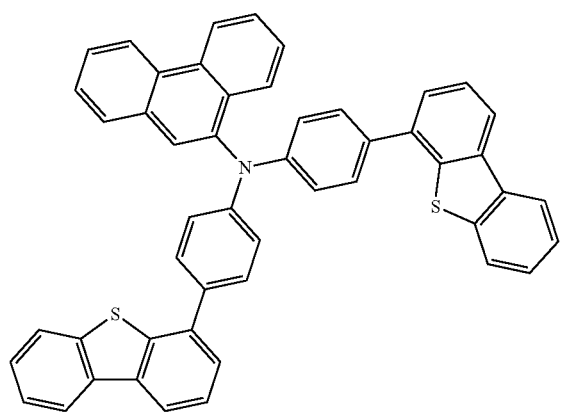
47
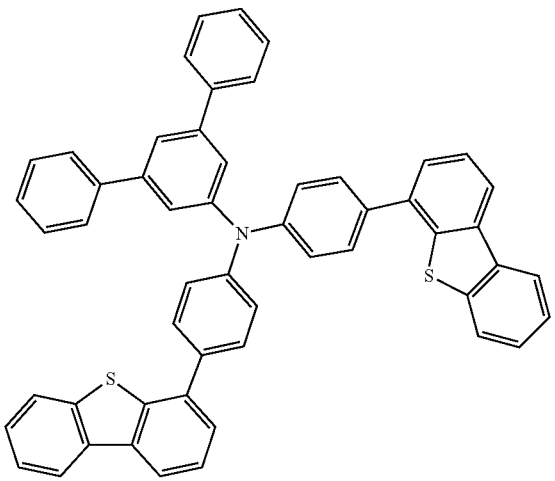
48
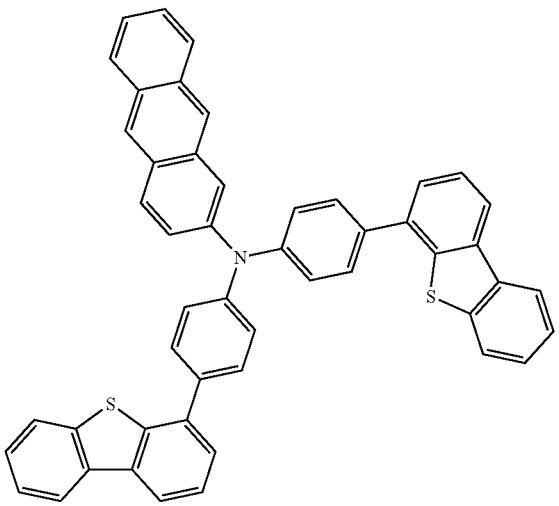
49
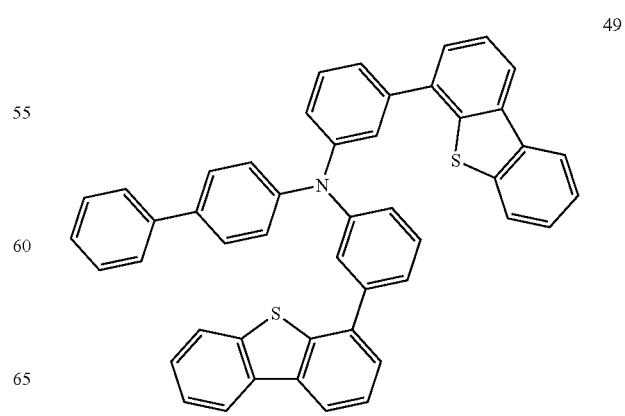

50
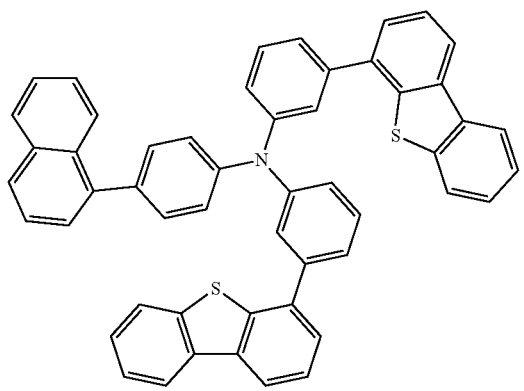
51
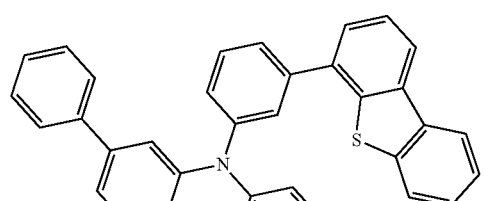
52
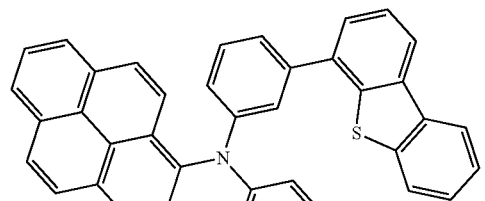
53
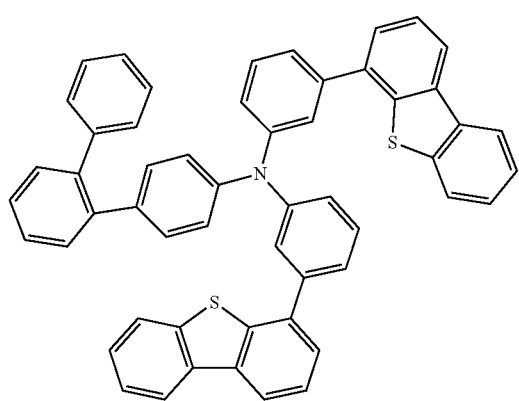
54
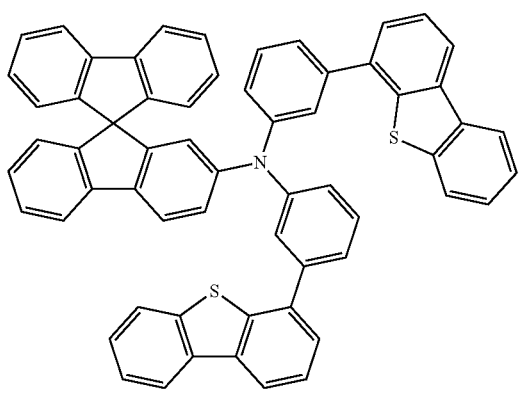
55
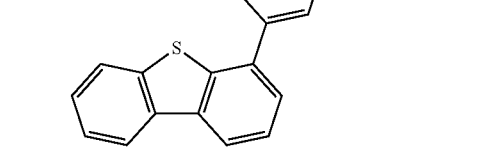
56
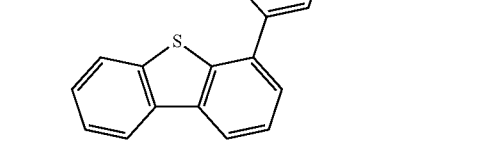

57
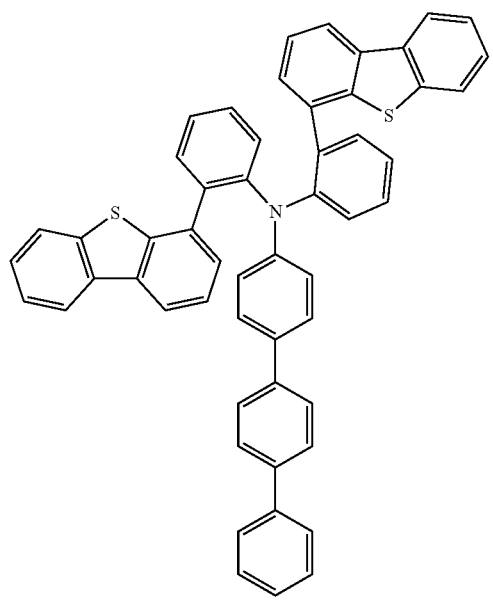
58
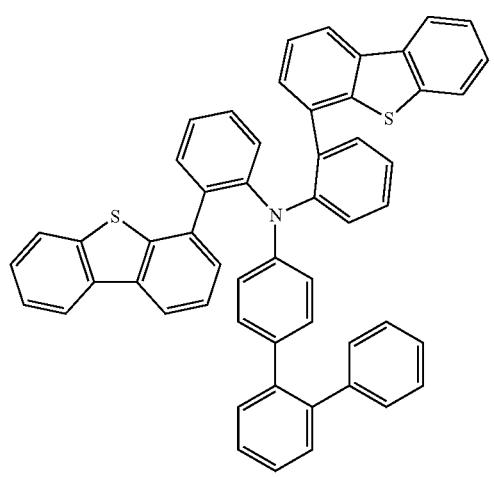
59
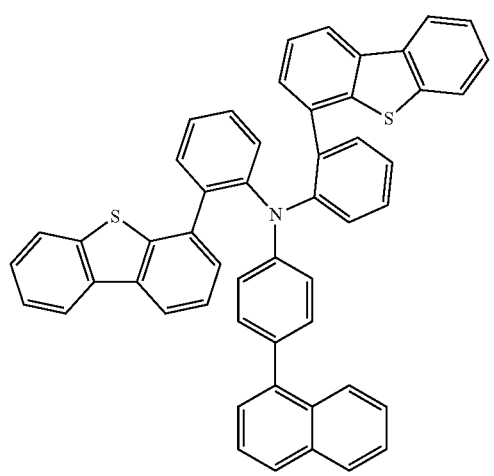
60
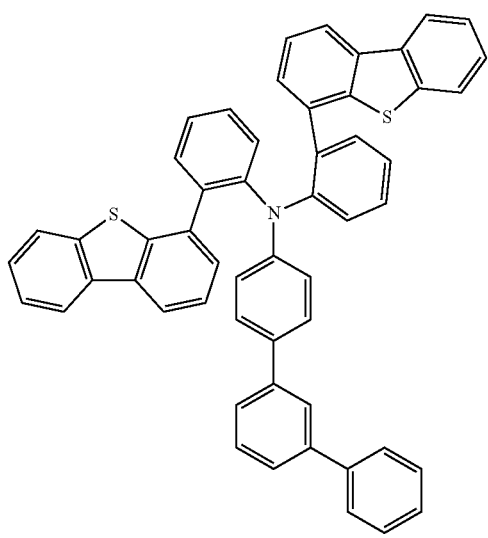
61
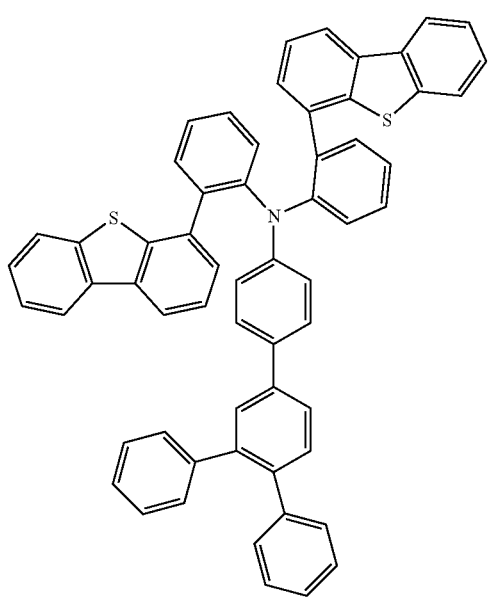
62
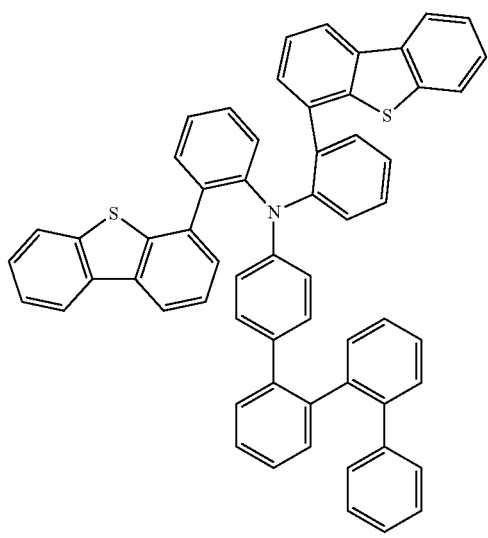

-continued

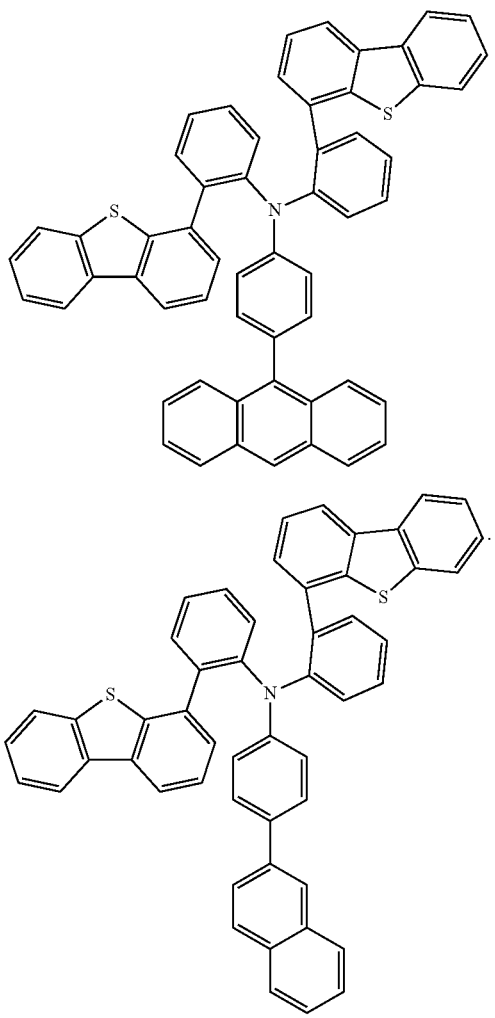

4. The organic light-emitting device of claim 1, wherein the at least one organic material layer comprises at least one layer selected from the group consisting of a hole injection layer, a hole transport layer, an auxiliary hole transport layer, a light-emitting layer, an auxiliary electron transport layer, an electron transport layer, and an electron injection layer.

5. The organic light-emitting device of claim 1, wherein the organic light-emitting device further comprises an encapsulating layer formed on the second electrode, and a barrier layer formed on the encapsulating layer.

6. The organic light-emitting device of claim 5, wherein the encapsulating layer is formed on entire faces of the second electrode.

7. The organic light-emitting device of claim 5, wherein the barrier layer is bonded to the encapsulating layer via an adhesive.

8. The organic light-emitting device of claim 1, wherein the organic light-emitting device further comprises a driving thin-film transistor including an active layer electrically connected to the first electrode.

9. The organic light-emitting device of claim 8, wherein the active layer includes an oxide semiconductor layer.

10. The organic light-emitting device of claim 8, wherein the driving thin-film transistor comprises a gate insulating film formed on the active layer, and a gate electrode formed on the gate insulating film.

* * * * *